US012642690B2

(12) United States Patent
Nicklas et al.

(10) Patent No.: US 12,642,690 B2
(45) Date of Patent: Jun. 2, 2026

(54) COLLAPSIBLE MENSES COLLECTING APPARATUS

(71) Applicant: Novva Biosolutions, LLC, Baltimore, MD (US)

(72) Inventors: Danielle Nicklas, Baltimore, MD (US); Alexis Lynn Lowe, Baltimore, MD (US); Andrew Mark Masteller, Quincy, MA (US); Clarissa Chenhui Ren, Baltimore, MD (US)

(73) Assignee: Novva Biosolutions, LLC, Baltimore, MD (US)

( * ) Notice: Subject to any disclaimer, the term of this patent is extended or adjusted under 35 U.S.C. 154(b) by 571 days.

(21) Appl. No.: 18/125,715

(22) Filed: Mar. 23, 2023

(65) Prior Publication Data

US 2023/0301820 A1 Sep. 28, 2023

Related U.S. Application Data

(60) Provisional application No. 63/323,162, filed on Mar. 24, 2022.

(51) Int. Cl.
*A61F 5/455* (2006.01)
*A61F 5/44* (2006.01)

(52) U.S. Cl.
CPC .......... *A61F 5/4553* (2013.01); *A61F 5/4404* (2013.01); *A61F 5/455* (2013.01)

(58) Field of Classification Search
CPC ....... A61F 5/4553; A61F 5/4404; A61F 5/455
See application file for complete search history.

(56) References Cited

U.S. PATENT DOCUMENTS 3,791,385 A * 2/1974 Davis ................. A61F 13/2051
604/12
5,476,455 A 12/1995 Silber
(Continued)

FOREIGN PATENT DOCUMENTS

WO WO 2014/015975 1/2014

OTHER PUBLICATIONS

"Flex Menstrual Cup Slim Fit Model," Amazon.com, First Available Jan. 11, 2020, 5 pages.
(Continued)

*Primary Examiner* — Guy K Townsend
(74) *Attorney, Agent, or Firm* — Sheridan Ross P.C.

(57) ABSTRACT

A menses collecting apparatus includes a basin and a closure. The basin may transition between a collapsed or folded state prior to insertion by a user and an expanded or unfolded state after insertion by the user. The menses collecting apparatus may be collapsible/closed radially prior to insertion by the user, and may collect menses in the expanded state after insertion by the user. The closure may also transition between an open configuration and a closed configuration. The closure may be collapsible/folded when transitioning between the open configuration and the closed configuration. When the basin is in the expanded state, the closure may also be in an open configuration or the closed configuration. The menses collecting apparatus may employ a tension-based mechanism to transition between the different basin states and closure configurations. The menses collecting apparatus may be configurable to fit within an applicator to assist in the insertion of the menses collecting apparatus.

20 Claims, 12 Drawing Sheets

(56)     References Cited

U.S. PATENT DOCUMENTS

| | | | |
|---|---|---|---|
| 6,332,878 B1 * | 12/2001 | Wray .................... | A61F 5/4556 |
| | | | 128/830 |
| 10,357,395 B2 | 7/2019 | Miller et al. | |
| 11,484,433 B1 * | 11/2022 | Miller .................. | A61F 5/4553 |
| 12,257,175 B2 * | 3/2025 | Shaviv ................. | A61F 5/4553 |
| 2021/0137725 A1 * | 5/2021 | Shaviv ................ | A61B 5/4337 |
| 2022/0331148 A1 * | 10/2022 | Miller .................. | A61F 5/4404 |
| 2023/0016976 A1 * | 1/2023 | Miller .................. | A61F 5/4553 |
| 2023/0301820 A1 * | 9/2023 | Nicklas ................ | A61F 5/4553 |
| 2024/0024153 A1 * | 1/2024 | Van Kempen ........ | A61F 5/4553 |
| 2025/0177191 A1 * | 6/2025 | Shaviv ..................... | A61F 6/08 |

OTHER PUBLICATIONS

International Search Report for International (PCT Patent Application No. PCT/US2023/016288, dated Jul. 3, 2023 12 pages.
International Preliminary Report on Patentability for International (PCT) Patent Application No. PCT/US2023/016288, dated Oct. 3, 2024 8 pages.

* cited by examiner

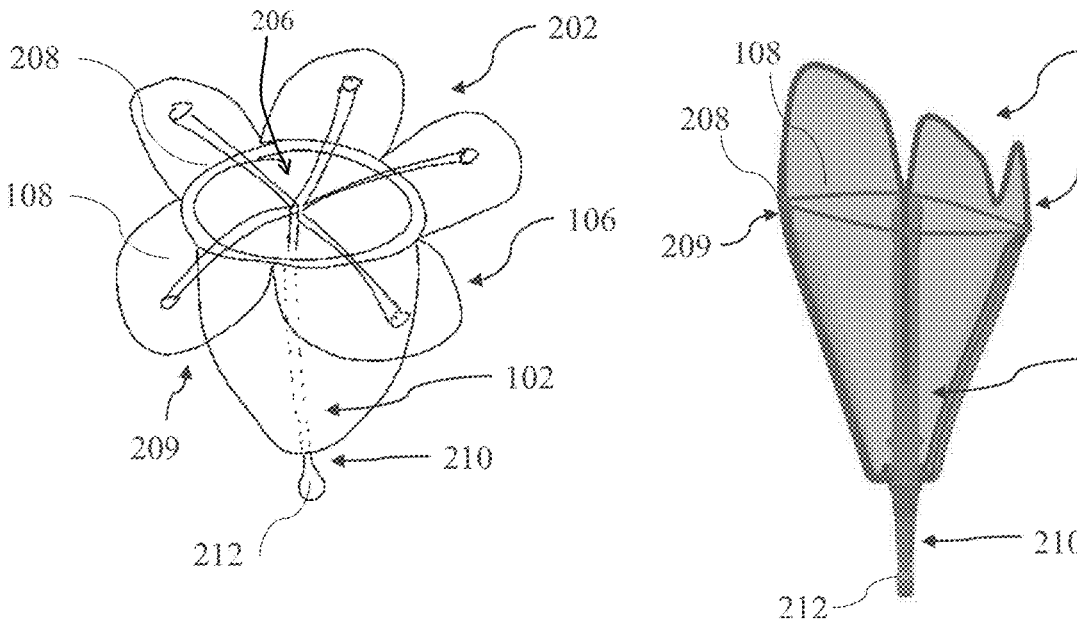
FIG. 2A
FIG. 2B
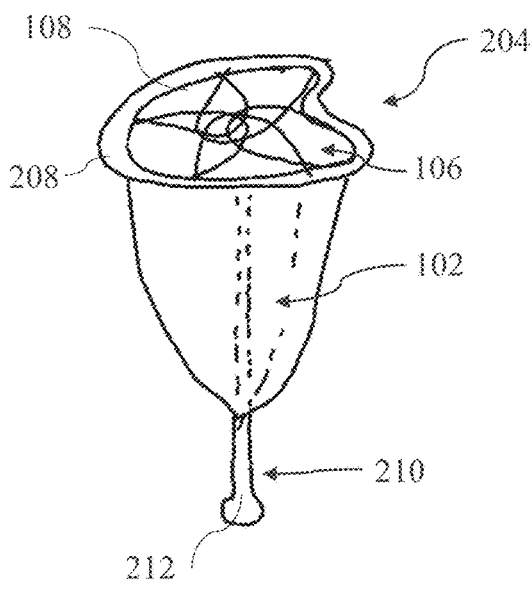
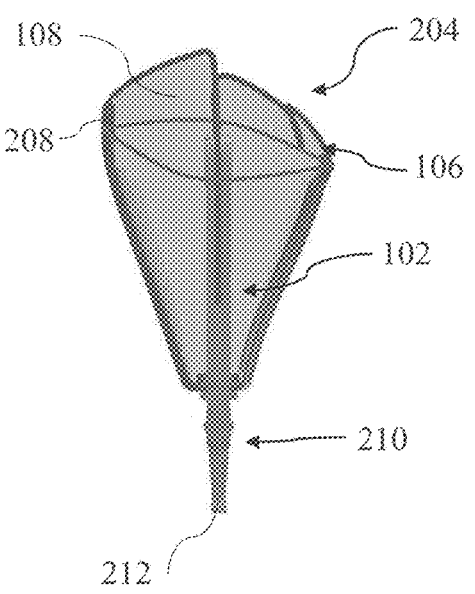
FIG. 2C
FIG. 2D

FIG. 3A                                    FIG. 3B

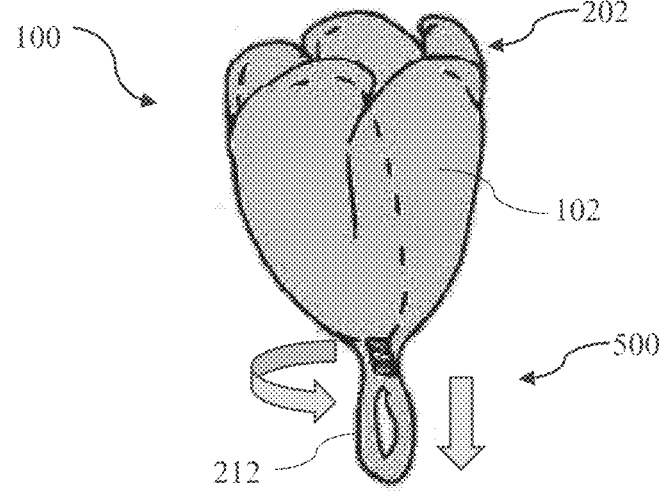
FIG. 5A
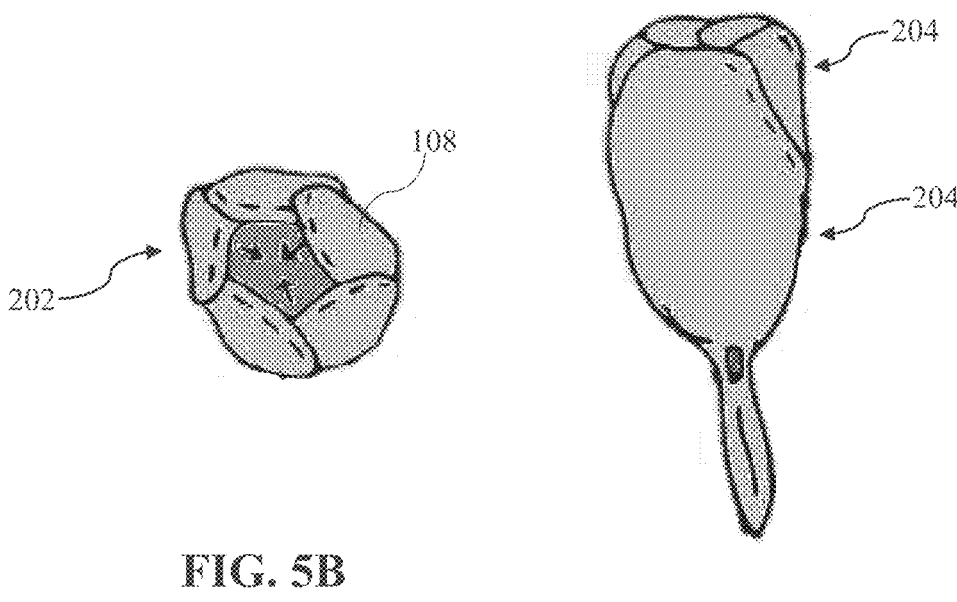
FIG. 5B
FIG. 5C

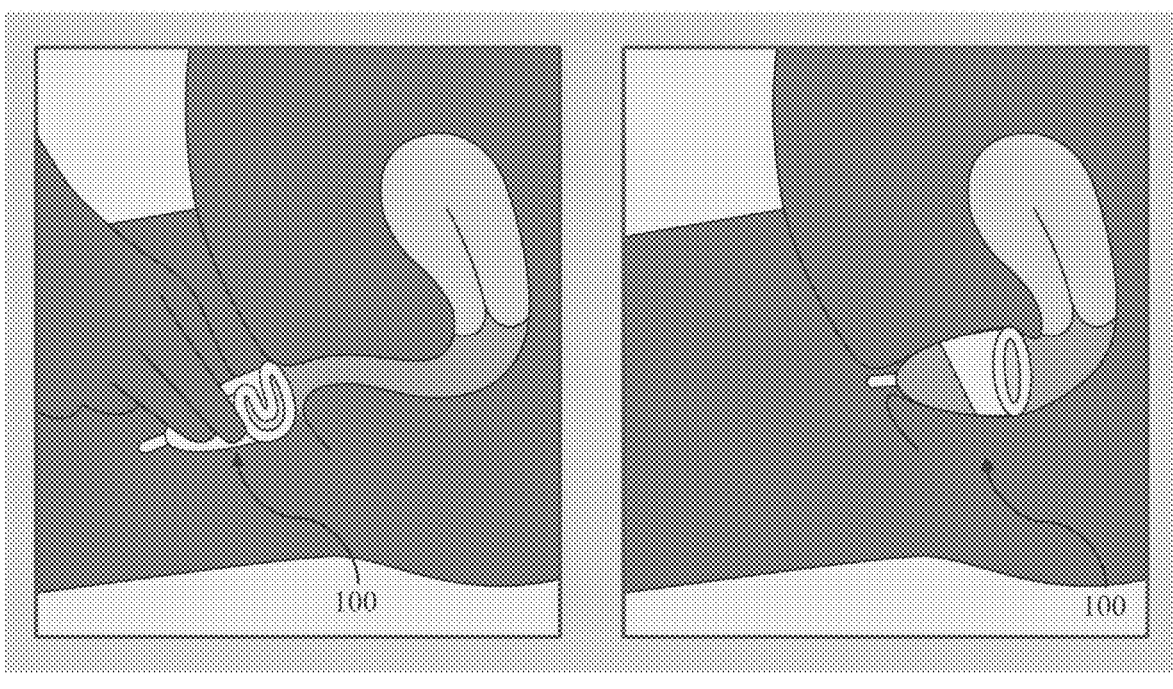
FIG. 9A
FIG. 9B
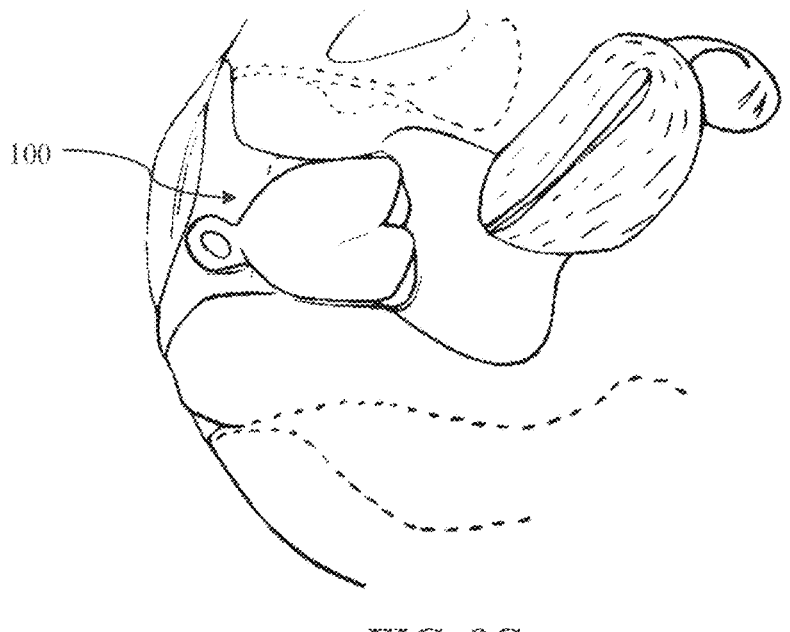
FIG. 9C

FIG. 9D    FIG. 9E

COLLAPSIBLE MENSES COLLECTING APPARATUS

CROSS-REFERENCE TO RELATED APPLICATIONS

This U.S. Non-Provisional patent application claims the benefit of priority of U.S. Provisional Patent Application Ser. No. 63/323,162, filed on Mar. 24, 2022, and entitled "NOVVACUP MENSTRUAL CUP", the entire disclosure of which is hereby incorporated by reference.

FIELD OF THE DISCLOSURE

The present disclosure relates generally to feminine hygiene products, and more specifically to a collapsible menses collecting apparatus. More specifically, the present disclosure relates to a collapsible menses collecting apparatus that includes a collapsible mechanism for containing collected menses.

BACKGROUND

Menstrual cups are a type of feminine hygiene product designed to collect menses discharged during females' menstrual period (e.g., blood, tissue, or mucosal membranes such as the endometrium or uterine lining, and other matter discharged during menstruation). Menstrual cups may be flexible and fabricated from latex, rubber, elastomer, or medical-grade silicone. Menstrual cups collect menses in a cavity defined by the walls of the basin of the menstrual cup. Traditionally, in order to use the menstrual cup, users must manually fold the walls of the menstrual cup by hand and maintain the folded shape while inserting the menstrual cup. Once inserted, further adjustment of the menstrual cup may be necessary to ensure correct positioning, users may need to twist and tug the menstrual cup by hand while the menstrual cup is located within a vagina. Because of the manual internal adjusting and movements, users may feel discomfort and resistance during this application process.

Menstrual cups work to catch and collect the menses within a defined cavity, as opposed to absorbing the menses like pads or tampons. The collective nature of the menstrual cups allows for them to be reusable (e.g., depending on the material from which the menstrual cup is fabricated). However, the collective nature also results in a heightened possibility of lack of containment during removal, as compared to pads or tampons. Because of the internal position and the structure of traditional menstrual cups, they cannot be folded or collapsed without risk of compacting the cavity and pushing the collected menses out. In addition, the cavity may largely remain open during removal, such that the collected menses may spill out during the removal process.

In this regard, it is desirable to provide an improved solution which allows for the reusable nature of the menstrual cup, which further provides an easy application and a level of containment and sealing during adjustment and removal of the inserted menstrual cup.

SUMMARY

There has been a long-felt and unmet need to provide a menses collecting apparatus that allows for easy application and safe containment and sealing during adjustment and removal without comprising the usable feature of menstrual cups. Embodiments of the present disclosure are directed to a menses collecting apparatus such as a menstrual cup or menstrual disc. In particular, embodiments of the present disclosure include a dynamically collapsible menstrual cup. In embodiments, the menstrual cup is configured to collapse prior to insertion, and to be inserted in a collapsed form. In embodiments, the menstrual cup may be inserted using an assistive applicator. In some embodiments, the menstrual cup comprises a floral cup including a closure (e.g., multiple flaps) that close by folding or rotating about an axis defined at the point of contact between the closure and the basin (e.g., the multiple flaps fold downward about the axis from an unfolded configuration to a folded configuration to contain the collected menses), and a basin portion that folds radially for insertion and removal. The cup and/or basin may include walls which form the cup and/or basin. When collapsed, the walls may be overlaid as layers (e.g., collapsed radially), which unfold after insertion to form a seal with the vaginal wall and provide access to a basin cavity defined within the basin. The seal may be a suction-based, fluid-impermeable barrier. The basin cavity may be configured to collect and contain menses. In some other embodiments, the menstrual cup comprises a cradle cup including a disc used to collect and secure collected menses.

In embodiments, the menstrual cup is configured to transition between a first state and at least a second state. Transitioning between the first and second states includes engaging in a tension-based mechanism (e.g., a spring, etc.). Using a small amount of applied tension, the walls (e.g., including, but not limited to, the lid and basin) of the menstrual cup stably fold inward. Alternatively, the application of tension may cause the walls of the menstrual cup to spring into a convex position (e.g., open state). Engaging the tension-based mechanism may activate a closure. The closure includes one or more sections that are open during the first state and closed during the second state. For example, the sections may have one or more flaps. The flaps may be open in the first state, either extended from a rim of the basin and at least partially touching the vaginal wall or alternatively extended from the rim of the basin and into the vaginal canal without touching the vaginal wall. The flaps may abut against one another when in the second state or, alternatively, the flaps may at least partially overlap when in the second state.

The tension-based mechanism may include a stem coupled to internal components within the basin and/or the closure. For example, the internal components may include a stem, where the stem is in communication with the closure. Upon engaging the stem, the closure may transition between the first and second states. For example, pulling the stem may cause the flaps to transition from the open position to the closed position. By way of another example, pushing the stem may cause the flaps to transition from the closed position to the open position. In embodiments, pulling and/or pushing the stem activates the tension-based mechanism to cause transition between the first and second states, wherein if the menstrual cup is in the first state (e.g., open) and the tension-based mechanism is activated, the menstrual cup will transition to the second state (e.g., closed). Conversely, if the menstrual cup is in the second state (e.g., closed) and the tension-based mechanism is activated, the menstrual cup will transition to the first state (e.g., open). That is to say activation of the tension-based mechanism will cause the menstrual cup to transition to the opposite state from the current state.

The stem may alternatively or in addition cause the basin to transition between an expanded and a collapsed configuration. For example, pulling the stem may cause the flaps to fold downward and the basin to fold into the collapsed position. Conversely, pushing the stem may cause the flaps to open upwards and the basin to open into an expanded position. For instance, pulling the stem may cause the basin to break a seal between a rim of the basin and the vaginal wall. By way of another example, pushing the stem may cause the flaps to open and the basin to unfold from the collapsed position.

By way of another example, the basin and closure may be a cradle cup including a disc with a unibody or single-piece design. The cradle cup may be fabricated from one or more layers of flexible materials including, but not limited to, an antimicrobial plastic, a medical-grade silicone, a suitable paper, fabric, rubber, or other materials. The cradle cup includes a tension-based mechanism comprising a tension-string wrapped around the basin and/or disc that is connected to an activator. The activator may be selected from a group including, but not limited to, a string, a pulling ring, a stem, or other activator.

It is noted the tension-based mechanism may include a stabilizing mechanical device which causes the closure to remain in the first state or the second state unless acted upon by the stem or other activator/actuator. The stabilizing mechanical device may be installed within the basin and/or the closure (e.g., a spring, detent, or other installed component). The stabilizing mechanical device may be integrated into the design of the basin and/or closure (e.g., a living hinge, or the like). In this regard, the first and second states may be considered stable absent an applied force, for purposes of the present disclosure.

For example, pulling on the stem may cause the open closure to begin to close. An opposite force is exerted against the stem until a predefined point in the transition from the first to the second state is achieved. At which point, the opposite force is no longer applied, and an assistive force is instead applied which may be standalone or combined with the pulling motion to complete the transition from the first state to the second state.

By way of another example, pushing or pulling on the stem may cause the closed closure to begin to open. An opposite force is exerted against the stem until a predefined point in the transition from the second to the first state is achieved. At which point, the opposite force is no longer applied, and an assistive force is instead applied that may be standalone or combined with the pushing motion to complete the transition from the second state to the first state.

In implementations, insertion and/or removal can involve the use of an applicator. The menstrual cup may be dimensioned to fit within the applicator when collapsed, such that the applicator is operable to receive the collapsed menstrual cup. The applicator includes one or more cavities. For example, the applicator may include a single basin cavity which contains the collapsed or folded menstrual cup. By way of another example, the applicator may include one or more multiple cavities configured to conform to aspects (e.g., folded wall portions or layers) of the menstrual cup to promote correct deployment (e.g., the correct unfolding and forming of a seal with the vaginal wall) after insertion and during removal of the applicator.

It is noted the menstrual cup and/or the applicator may be fabricated from one or more layers of a flexible or rigid material including, but not limited to, an antimicrobial plastic, a medical-grade silicone, a suitable paper, fabric, or rubber, or other material.

A number of variations and modifications of the foregoing disclosure can be used. It would be possible to provide for some features of the disclosure without providing others.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and/or reducing cost of implementation.

In one aspect, the present disclosure includes a dynamically collapsible menstrual cup comprising: a basin for collecting menses; a stem attached along the length of the basin; and a tension-based mechanism that is controlled by pulling the stem, wherein when the stem is under tension the basin transitions from a first stable state to a second stable state or from the second stable state to the first stable state when released from outside tension.

In some embodiments, the first stable state is open. In some embodiments, the second stable state is collapsed.

In another aspect, the dynamically collapsible menstrual cup, further comprises a secure closure to contain the collected menses. In some embodiments, the secure closure collapses by folding or rotating about an axis defined at the point of contact between the closure and the basin to contain the collected menses. In some embodiments, the secure closure is connected to and activated by the tension-based mechanism. In some embodiments, the secure closure comprises one or more sealable silicone flaps that fold downward.

In one aspect, the dynamically collapsible menstrual cup further comprises one or more flaps that fold downward to contain the collected menses. In some embodiments, the basin forms a complete, circumferential seal along vaginal walls when in an open state.

In some embodiments, the dynamically collapsible menstrual cup further comprises a closure that collapses by folding or rotating about an axis defined at the point of contact between the closure and the basin.

In some embodiments, the basin is collapsible radially. In some embodiments, the tension-based mechanism is activated with a tug downwards (away from the basin) on the stem. In some embodiments, the tension-based mechanism is activated with a second tug downwards (away from the basin) on the stem causing the basin to open and create a seal along a vaginal wall. In some embodiments, the tension-based mechanism is activated with a push upwards or release of tension on the stem causing the basin to open and create a seal along a vaginal wall. In some embodiments, the tension-based mechanism is activated with a tug downwards on the stem causing the basin to collapse and simultaneously break the seal holding the basin in place. In some embodiments, the tension-based mechanism is activated with a tug downwards on the stem causing: the basin to collapse, simultaneously breaking a seal holding the basin in place; and the secure closure to activate to contain the collected menses.

In some embodiments, the basin is constructed of a medical grade silicone. In some embodiments, the first state is open, and the second state is collapsed.

In another aspect, the present disclosure includes a dynamically collapsible menstrual cup comprising: a basin for collecting menses; a stem attached along the length of the basin; a tension-based mechanism that is activated by pulling the stem, wherein when the tension is applied the basin goes from a first stable state to a second stable state or from the second stable state to the first stable state when tension is released; and a secure closure to contain the collected menses, wherein the secure closure is connected to and activated by the tension-based mechanism. In some embodiments, the secure closure comprises one or more sealable silicone flaps. In some embodiments, the first stable state is collapsed, and wherein the second stable state is open.

In another aspect, the present disclosure includes dynamically collapsible menstrual cup comprising: a basin for collecting menses; a stem attached to along the length of the basin; a tension-based mechanism that is activated by pulling the stem, wherein when the tension is applied the basin goes from a first state to a second state or from the second state to the first state when tension is released; and one or more sealable silicone flaps that close to contain the collected menses, wherein the one or more sealable silicone flaps is connected to and activated by the tension-based mechanism. In some embodiments, the first state is open, and the second state is closed. In some embodiments, when the dynamically collapsible menstrual cup is collapsed, the one or more sealable silicone flaps is closed.

In some embodiments, the dynamically collapsible menstrual cup further comprises an applicator for insertion and/or removal of the dynamically collapsible menstrual cup, and controlling the tension-based mechanism for collapsing and closure of the one or more secure flaps during removal and/or insertion. In some embodiments, the dynamically collapsible menstrual cup further comprises a cleaning kit for the dynamically collapsible menstrual cup.

In another aspect, the present disclosure includes an applicator for insertion and/or removal of a dynamically collapsible menstrual cup. In another aspect, the present disclosure includes a compatible device for insertion and/or removal of a dynamically collapsible menstrual cup. In another aspect, the present disclosure includes a cleaning kit for a dynamically collapsible menstrual cup. In another aspect, the present disclosure includes a dynamically collapsible menstrual cup as described herein. In another aspect, the present disclosure includes a method of manufacturing a collapsible menstrual cup as described herein. A collapsible menstrual cup as described herein. In another aspect, to the present disclosure includes a collapsible menstrual cup including a collapsible closure.

In another aspect, the present disclosure includes a menses collecting apparatus with a basin for collecting menses. The apparatus includes one or more basin walls and a basin cavity defined within the one or more basin walls, where the basin is operable to receive and collect menses within the basin cavity when the apparatus is in a first stable state, and is operable to be removed while containing the collected menses within the basin cavity when the apparatus is in a second stable state. The apparatus includes a closure coupled to the basin. The apparatus includes a tension-based mechanism including an activator, where the activator is operable to cause the apparatus to transition between an open configuration in which the basin cavity receives and collects the menses and a closed configuration operable to contain the menses within the basin cavity after basin cavity receives and collects the collected menses.

In some embodiments, the menses collecting apparatus comprises a menstrual disc.

In some embodiments, the basin is open and expanded and the apparatus is in the open configuration in the first stable state, and the basin is open and expanded and the apparatus is in the closed configuration in the second stable state.

In some embodiments, the activator is coupled to the closure, and the closure folds during transition between the open configuration and the closed configuration at a location where the closure couples to the basin. In some embodiments, the closure includes one or more flaps that fold downward during a transition from the open configuration to the closed configuration. In some embodiments, the apparatus further includes a rim at the location where the closure couples to the basin.

In some embodiments, the apparatus is operable to be inserted into a user in a third state, where the basin and the closure is folded and collapsed in the third state.

In some embodiments, the tension-based mechanism is actuatable via the activator to cause the apparatus to transition from the third state to the first stable state, and the apparatus creates a seal with a vaginal wall of the user during the transition. In some embodiments, the tension-based mechanism is actuatable via the activator to cause the apparatus to transition from the first stable state to the second stable state, and the apparatus breaks the seal with the vaginal wall during the transition. In some embodiments, the basin forms a complete, substantially circumferential seal along vaginal walls when in the first stable state.

In some embodiments, the basin is collapsible radially to be folded and collapsed into the third state. In some embodiments, the apparatus is at least partially insertable into an applicator for use during insertion of the menses collecting apparatus into the user when in the third state.

In some embodiments, the activator is a stem, a pulling ring, or a string. In some embodiments, the basin is a single-piece cup including the one or more basin walls. In some embodiments, the basin is a single-piece cradle-shaped disc including the one or more basin walls.

In some embodiments, the apparatus further includes a cap in communication with the activator. The activator is operable to cause the cap to transition from an open position and a closed position, where the cap is configured to close an opening within the closure when the apparatus is in the closed configuration to contain the menses within the basin cavity after the basin cavity receives and collects the collected menses.

In another aspect, the present disclosure includes a system with a menses collecting apparatus. The apparatus includes a basin for collecting menses. The basin includes one or more basin walls, and a basin cavity defined within the one or more basin walls, where the basin is operable to receive and collect menses within the basin cavity when the apparatus is in a first stable state, and is operable to be removed while containing the collected menses within the basin cavity when the apparatus is in a second stable state. The apparatus includes a closure coupled to the basin. The apparatus includes a tension-based mechanism including an activator, where the activator is operable to cause the apparatus to transition between an open configuration in which the basin cavity receives and collects the menses and a closed configuration operable to contain the menses within the basin cavity after the basin cavity receives and collects the collected menses. The system includes an applicator operable to receive the menses collecting apparatus when in a third state and insert the menses collecting apparatus into a user in the third state prior to the receiving and collecting of menses when the menses collecting apparatus is in the first stable state.

In some embodiments, the applicator comprises a first connecting component and the menses collecting apparatus includes a corresponding second connecting component, where the first connecting component is operable to engage the corresponding second connecting component. In some embodiments, the first connecting component and the corresponding second connecting components are components of an interlocking assembly or are magnetic.

In another aspect, the present disclosure is directed to the manufacture of a menses collecting apparatus.

In another aspect, the present disclosure is directed to a method. The method may include, but is not limited to, collecting menses with a menses collecting apparatus. The apparatus includes a basin for collecting menses. The basin includes one or more basin walls, and a basin cavity defined within the one or more basin walls, where the basin in a first stable state, and where the basin is operable to receive and collect menses within the basin cavity when the apparatus is in the first stable state. The apparatus includes a closure coupled to the basin. The apparatus includes a tension-based mechanism including an activator, where the activator is operable to cause the apparatus to transition between an open configuration in which the basin cavity receives and collects the menses and a closed configuration operable to contain the menses within the basin cavity after the basin cavity receives and collects the collected menses. The method may include, but is not limited to, actuating the tension-based mechanism via the activator to cause the menses collecting apparatus to transition from the first stable state to a second stable state, where the activator is operable to cause the apparatus to transition between the open configuration and the closed configuration, and where the basin is operable to be removed while containing the collected menses within the basin cavity when the apparatus is in the second stable state.

In some embodiments, the method may include, but is not limited to, loading the menses collecting apparatus into an applicator prior to collecting the menses, where the menses collecting apparatus is in a third state when loaded into the applicator, and where the basin and the closure is folded and collapsed when the menses collecting apparatus in the third state.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

The term "a" or "an" entity, as used herein, refers to one or more of that entity. As such, the terms "a" (or "an"), "one or more" and "at least one" can be used interchangeably herein.

The transitional term "comprising" is synonymous with "including," "containing," or "characterized by," is inclusive or open-ended and does not exclude additional, unrecited elements or method steps.

Unless otherwise indicated, all numbers expressing quantities, dimensions, conditions, ratios, ranges, and so forth used in the specification and claims are to be understood as being modified in all instances by the term "about" or "approximately". Accordingly, unless otherwise indicated, all numbers expressing quantities, dimensions, conditions, ratios, ranges, and so forth used in the specification and claims may be increased or decreased by approximately 5% to achieve satisfactory results. Additionally, where the meaning of the terms "about" or "approximately" as used herein would not otherwise be apparent to one of ordinary skill in the art, the terms "about" and "approximately" should be interpreted as meaning within plus or minus 5% of the stated value.

All ranges described herein may be reduced to any sub-range or portion of the range, or to any value within the range without deviating from the invention. For example, the range "5 to 55" includes, but is not limited to, the sub-ranges "5 to 20" as well as "17 to 54."

The use of "substantially" in the present disclosure, when referring to a measurable quantity (e.g., a diameter or other distance) and used for purposes of comparison, is intended to mean within 5% of the comparative quantity. The terms "substantially similar to," "substantially the same as," and "substantially equal to," as used herein, should be interpreted as if explicitly reciting and encompassing the special case in which the items of comparison are "similar to," "the same as" and "equal to," respectively.

The transitional phrase "consisting of" excludes any element, step, or ingredient not specified in the claim, but does not exclude additional components or steps that are unrelated to the disclosure such as impurities ordinarily associated therewith.

The transitional phrase "consisting essentially of" limits the scope of a claim to the specified materials or steps and those that do not materially affect the basic and novel characteristic(s) of the claimed invention.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

The preceding is a simplified summary of the disclosure intended to provide an understanding of some aspects of the settler devices of this disclosure. This Summary is neither an extensive nor exhaustive overview of the invention and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below. As will be appreciated, other embodiments are possible using, alone or in combination, one or more of the features set forth above or described herein. For example, it is contemplated that various features and devices shown and/or described with respect to one embodiment may be combined with or substituted for features or devices of other embodiments regardless of whether or not such a combination or substitution is specifically shown or described herein. Additional aspects of the present invention will become more readily apparent from the Detailed Description, particularly when taken together with the drawings.

BRIEF DESCRIPTION OF FIGURES

Those of skill in the art will recognize that the following description is merely illustrative of the principles of the disclosure, which may be applied in various ways to provide many different alternative embodiments. This description is made for illustrating the general principles of the teachings of this disclosure and is not meant to limit the inventive concepts disclosed herein.

The accompanying drawings, which are incorporated in and constitute a part of the specification, illustrate embodiments of the disclosure and together with the general description of the disclosure given above and the detailed description of the drawings given below, serve to explain the principles of the disclosure.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

Figure 1:
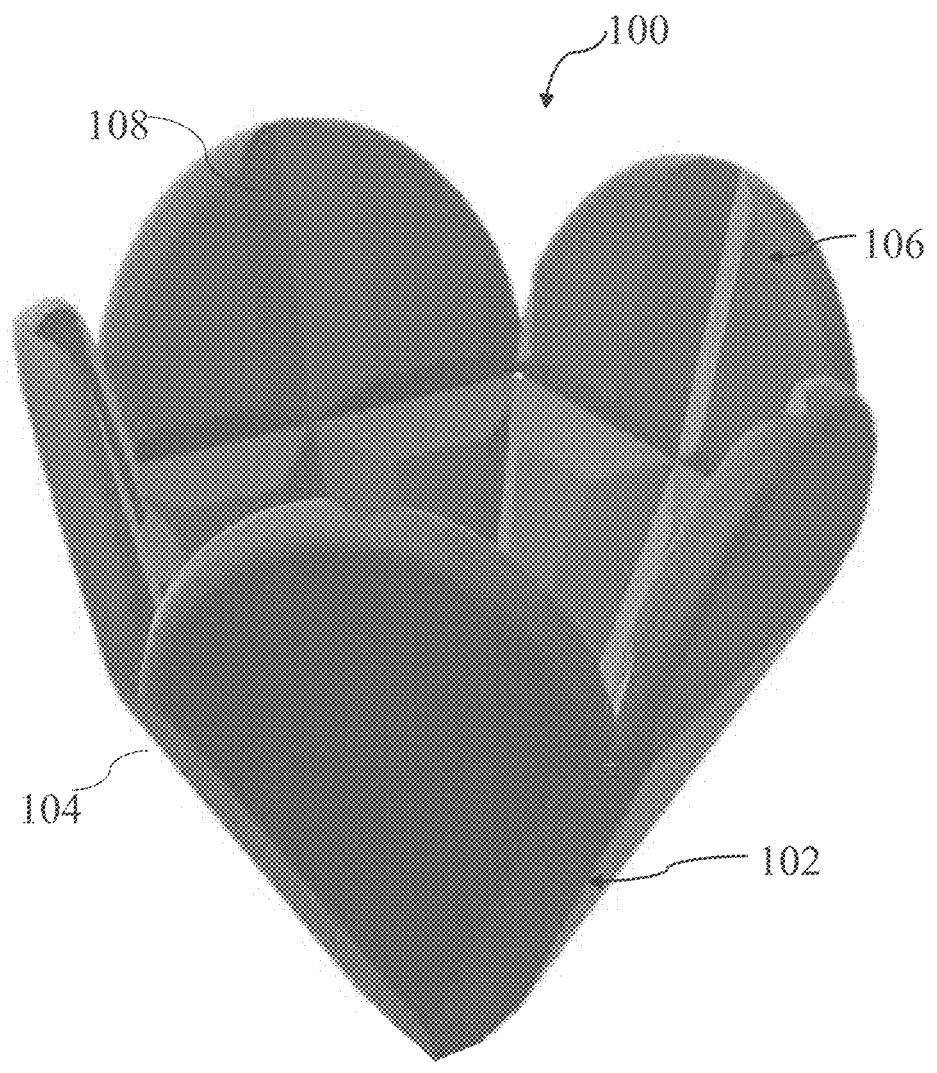
Figure 3C:
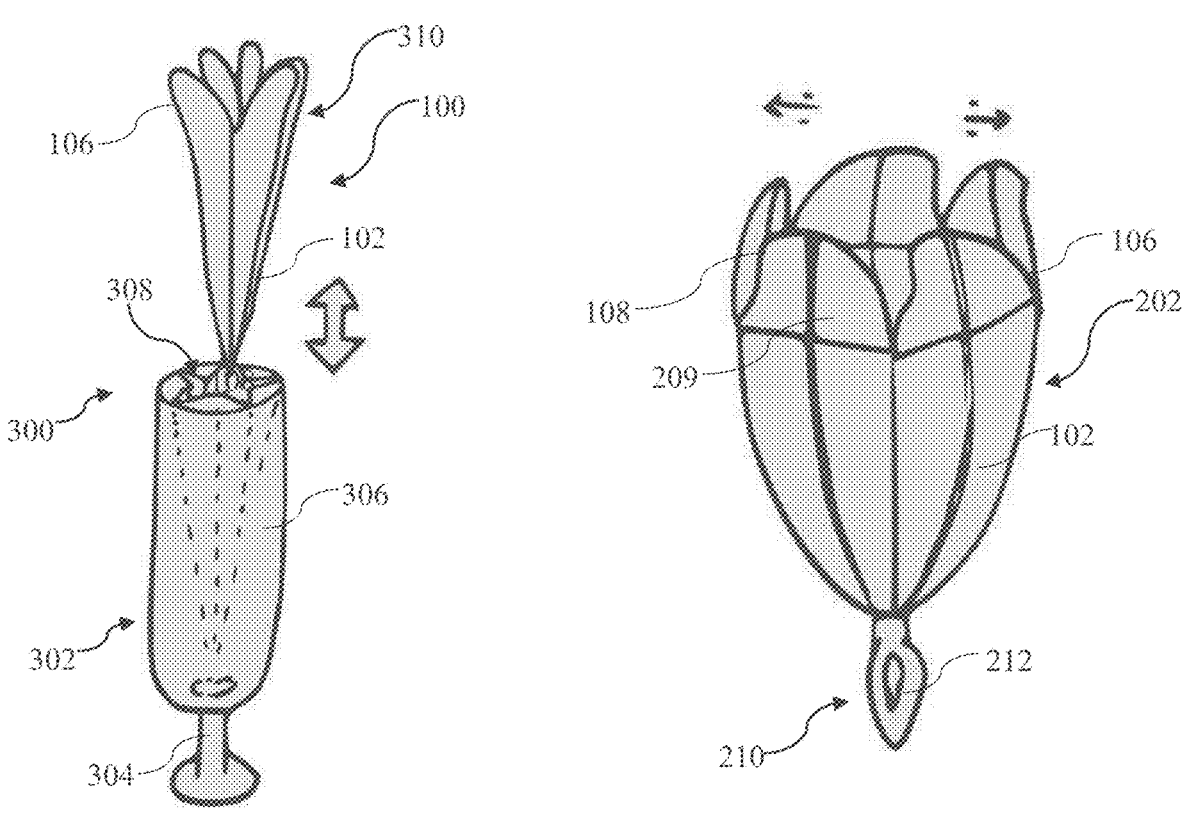
Figure 3C:
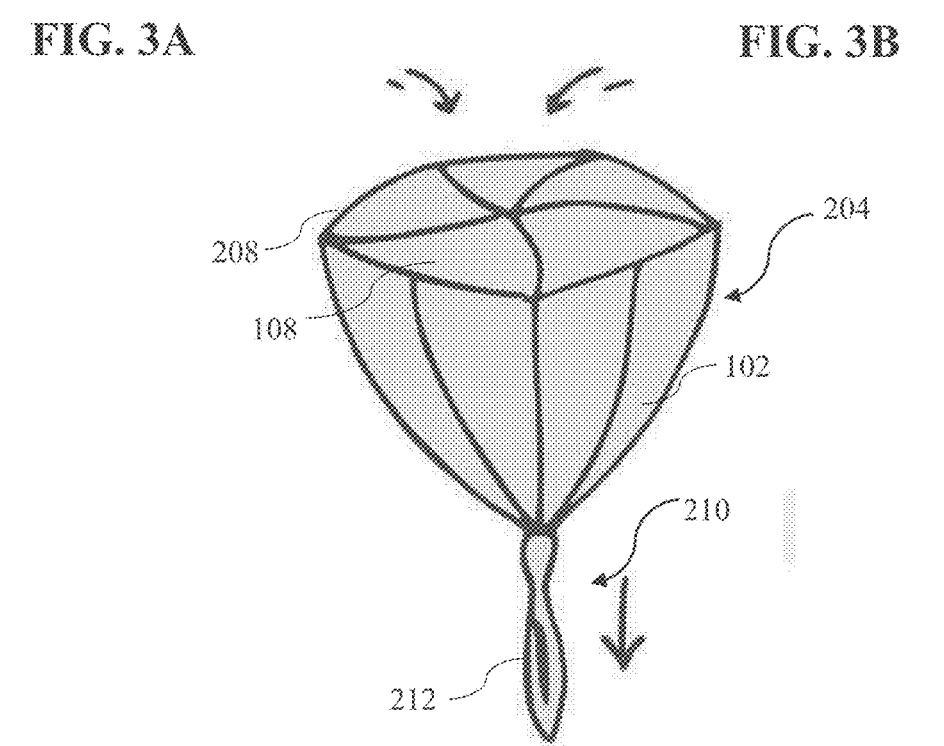
Figures 4A, 4B, 4C, 4D:
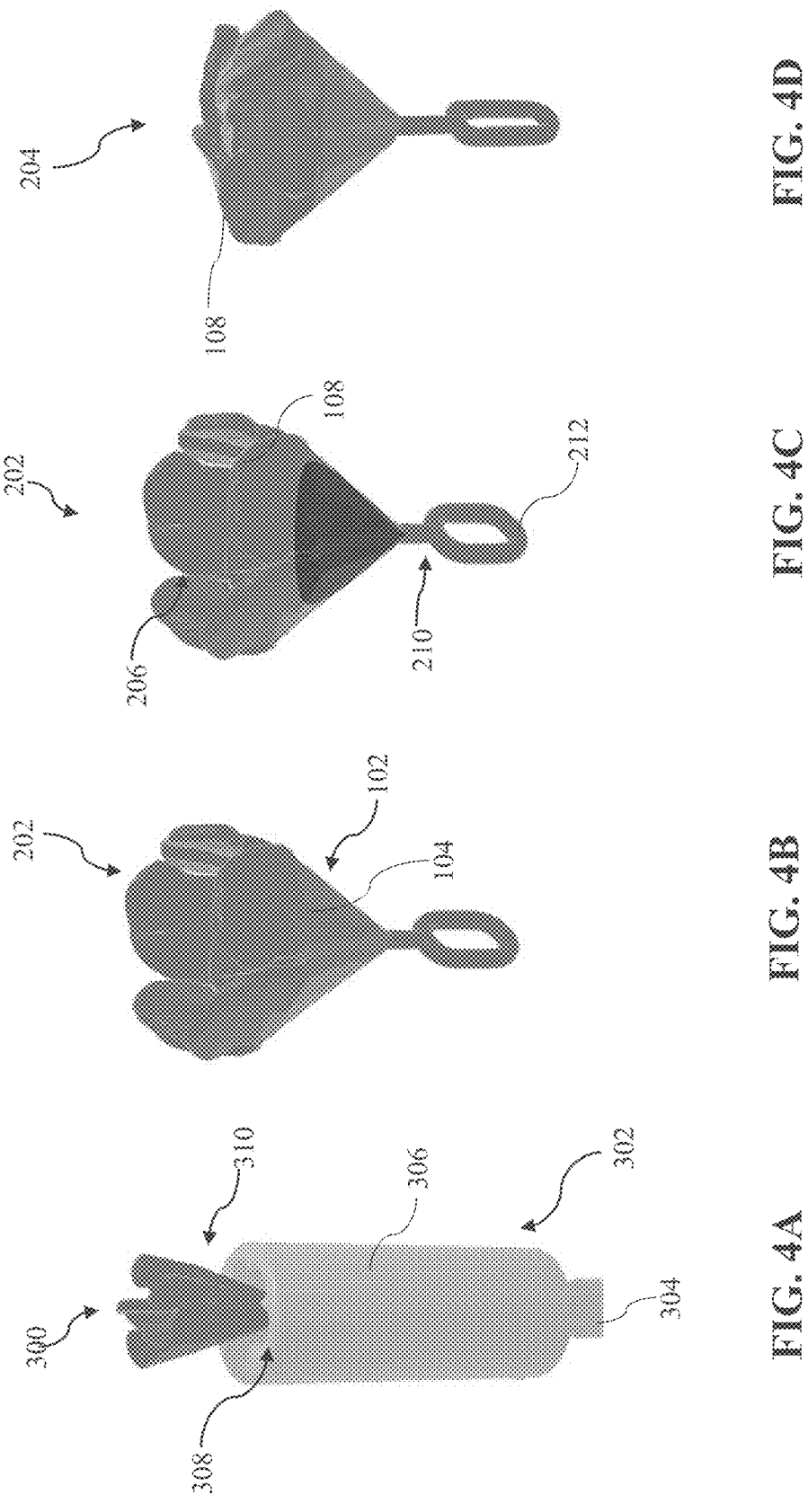
Figures 6A, 6B, 6C:
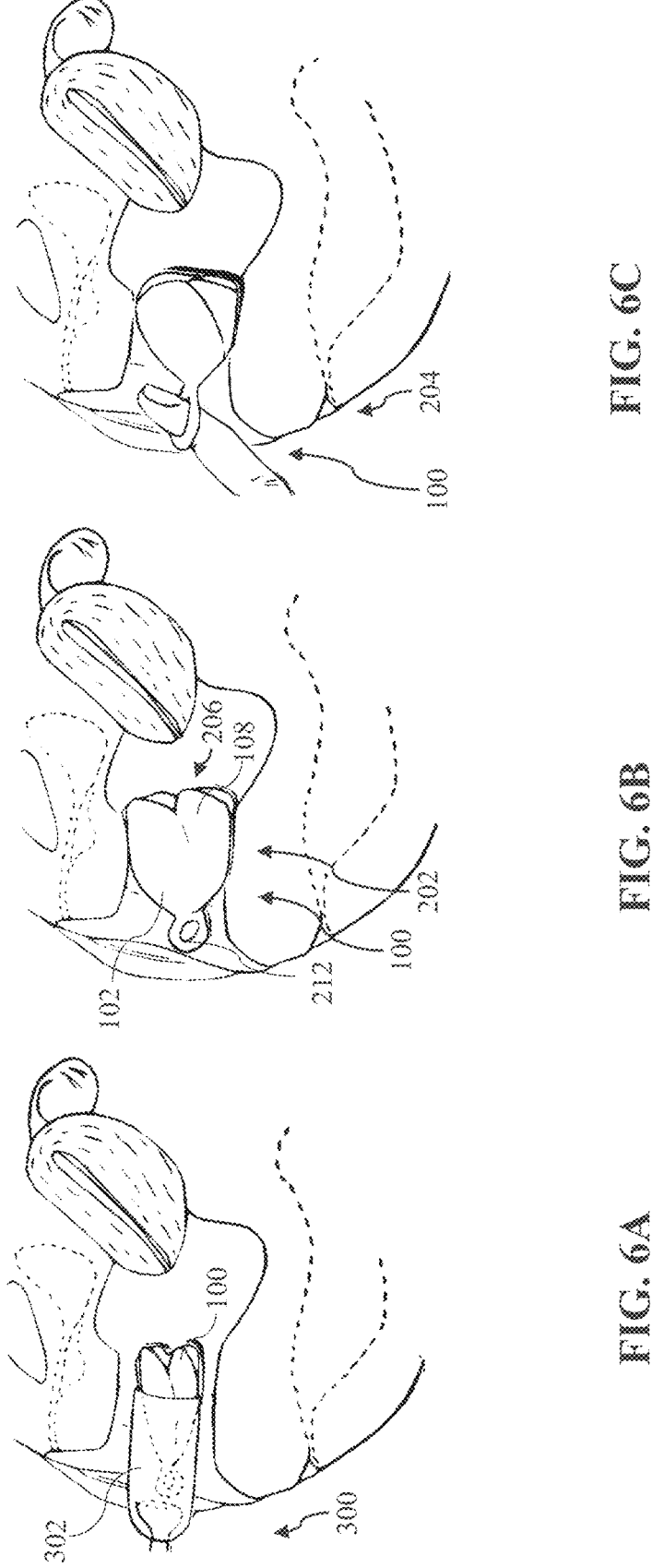
Figures 7A, 7B, 7C:
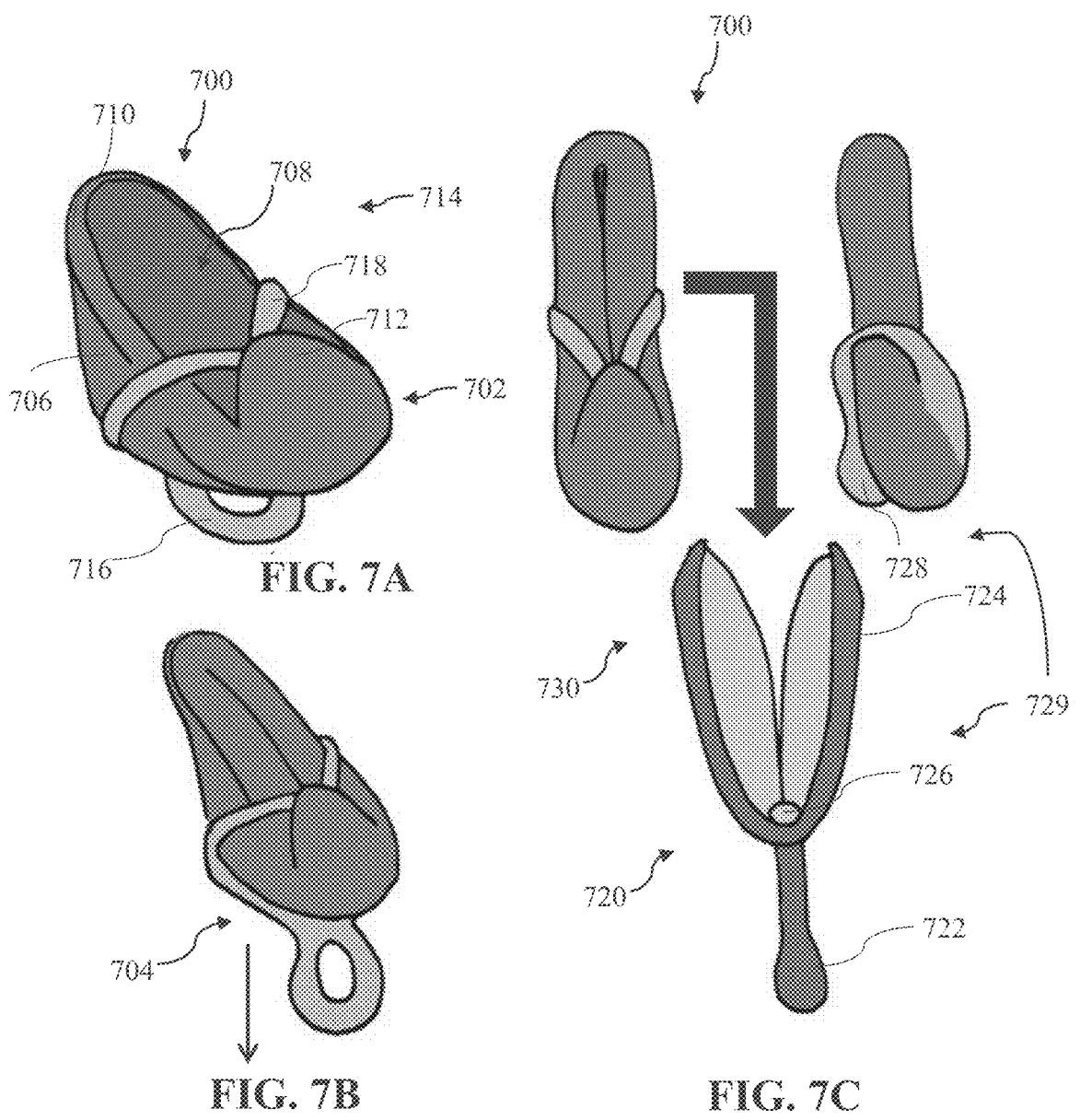
Figures 8A, 8B, 8C:
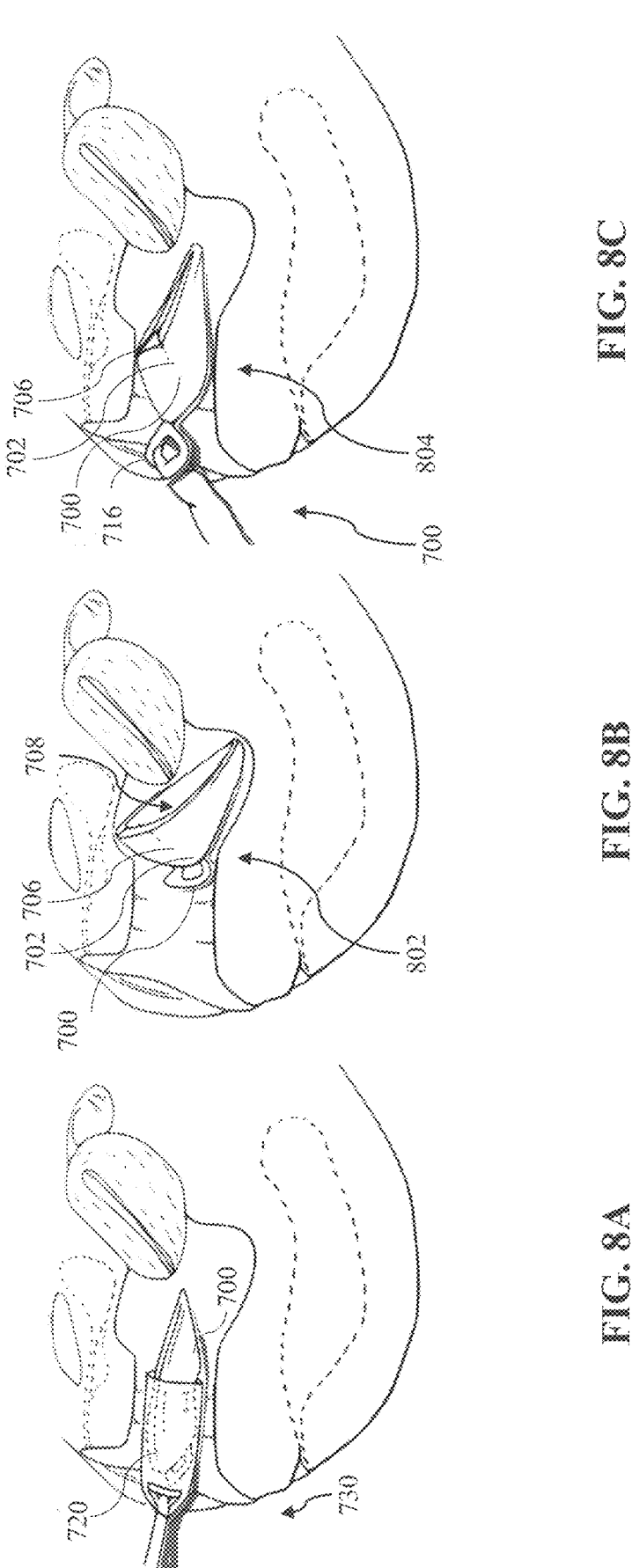
Figure 9F:
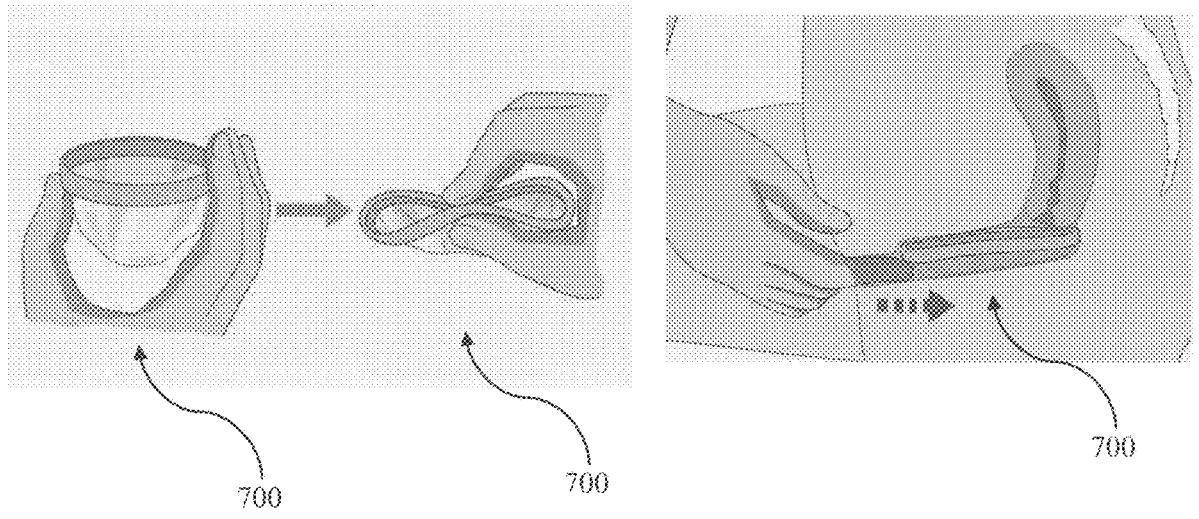
Figure 9F:
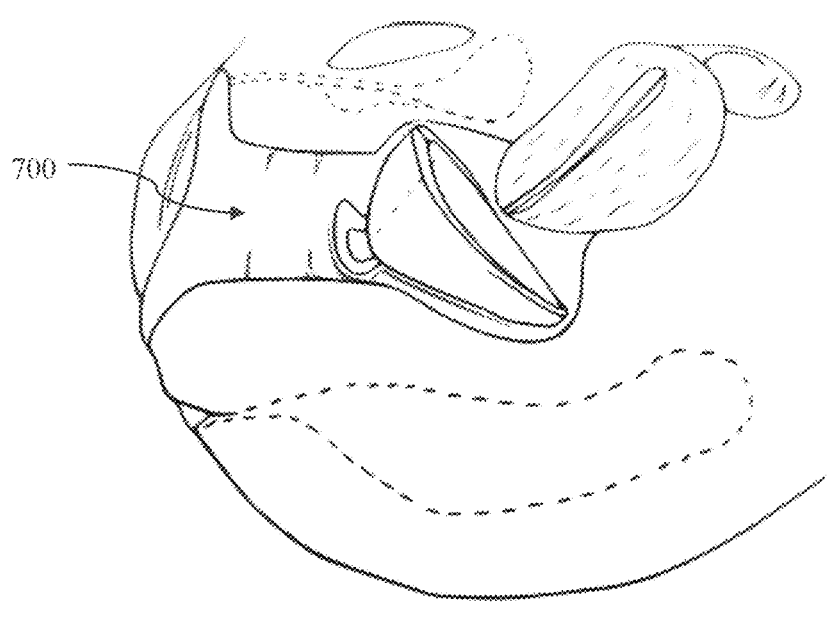
Figures 10A, 10B:
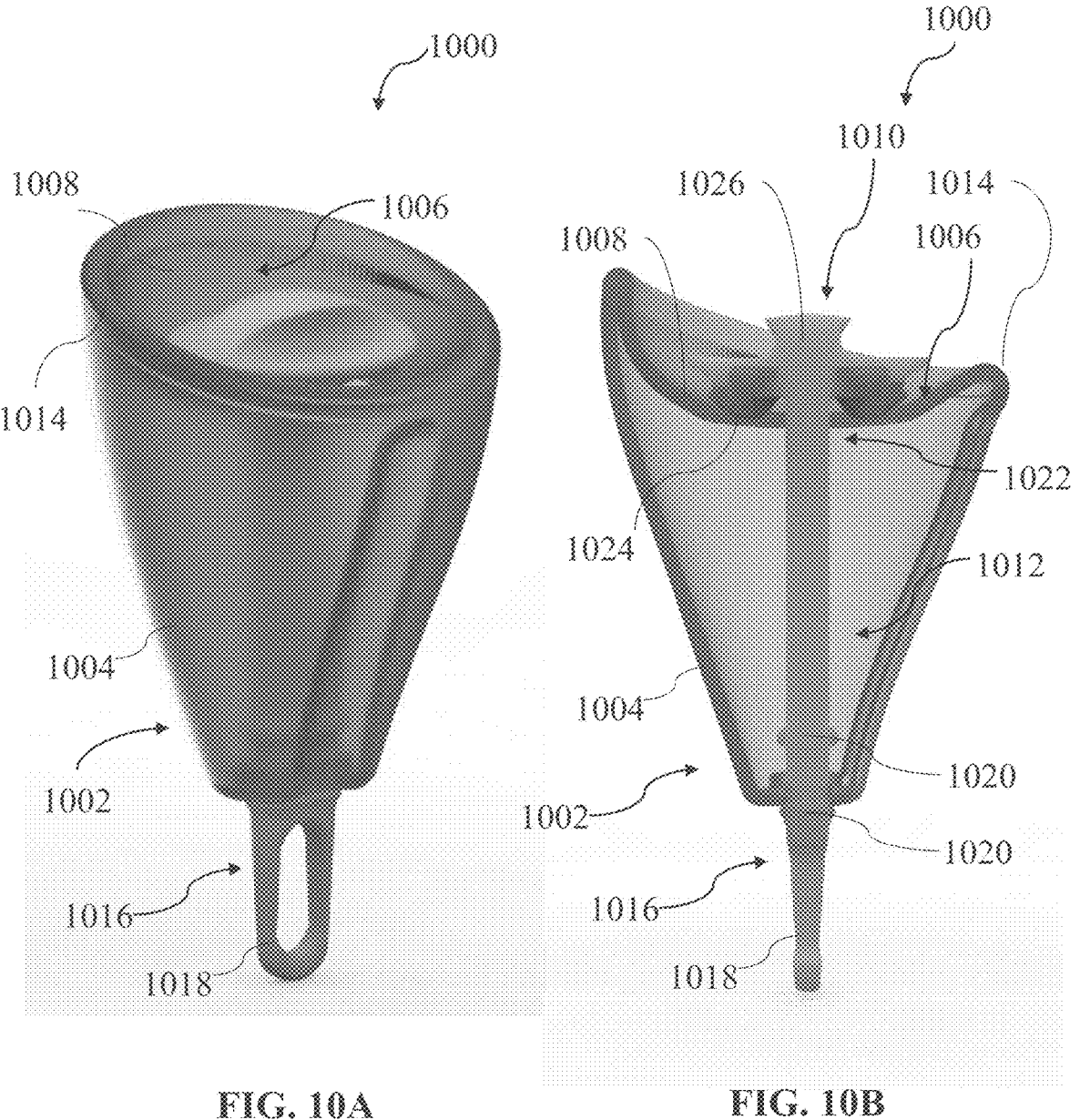
Figures 11A, 11B, 11C:
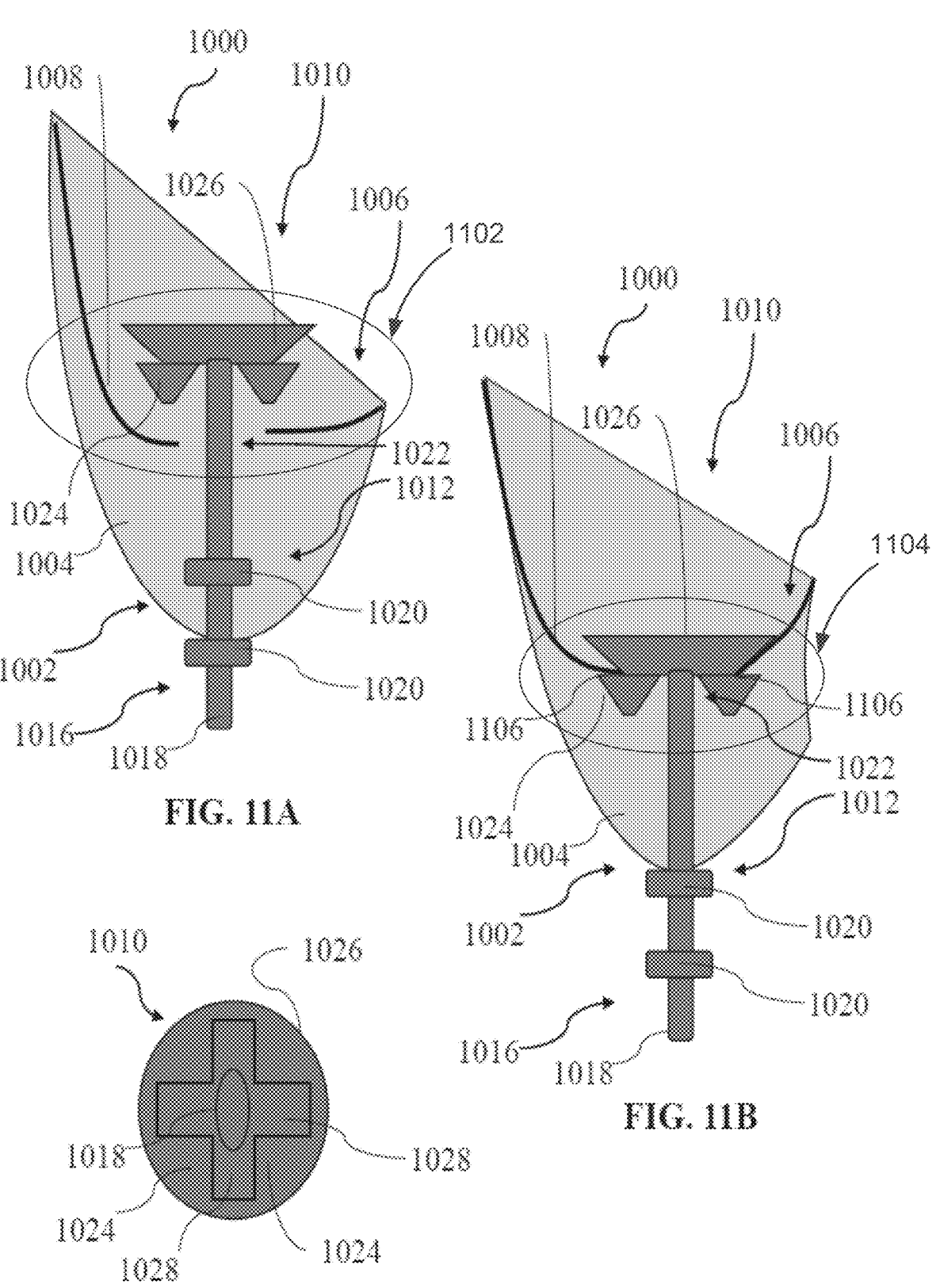

FIG. 1 depicts a perspective view of a collapsible floral menstrual cup, in accordance with embodiments of the present disclosure;

FIG. 2A depicts a perspective view of the collapsible floral menstrual cup of FIG. 1 in an open state, in accordance with embodiments of the present disclosure;

FIG. 2B depicts a side elevation view of the collapsible menstrual cup of FIG. 2A in the open state, in accordance with embodiments of the present disclosure;

FIG. 2C depicts a perspective view of the collapsible menstrual cup of FIG. 2A in a closed state, in accordance with embodiments of the present disclosure;

FIG. 2D depicts a side elevation view of the collapsible menstrual cup of FIG. 2C in the closed state, in accordance with embodiments of the present disclosure;

FIG. 3A depicts the collapsible floral menstrual cup of FIG. 1 and an assistive applicator, in accordance with embodiments of the present disclosure;

FIG. 3B depicts a perspective view of the collapsible floral menstrual cup of FIG. 3A activated by a tension mechanism after transitioning to an open state with open flaps and expanded basin, in accordance with embodiments of the present disclosure;

FIG. 3C depicts a perspective view of the collapsible floral menstrual cup of FIG. 3A activated by a tension mechanism after transitioning from the open state of FIG. 3B to a closed state with closed flaps and expanded basin, in accordance with embodiments of the present disclosure;

FIG. 4A depicts the collapsible floral menstrual cup of FIG. 1 at least partially within the assistive applicator of FIG. 3A, in accordance with embodiments of the present disclosure;

FIG. 4B depicts the collapsible floral menstrual cup in FIG. 4A activated by the assistive activator, and in an open state with open flaps and expanded basin for receiving menses, in accordance with embodiments of the present disclosure;

FIG. 4C depicts the collapsible floral menstrual cup at the open state of FIG. 4B receiving menses, in accordance with embodiments of the present disclosure;

FIG. 4D depicts the collapsible floral menstrual cup containing and sealing menses in a closed state with closed flaps and expanded state after receiving menses in FIG. 4C, in accordance with embodiments of the present disclosure;

FIG. 5A depicts a perspective view of the collapsible floral menstrual cup of FIG. 1 in an open state with open flaps and expanded basin, in accordance with embodiments of the present disclosure;

FIG. 5B depicts a top view of the collapsible floral menstrual cup in the closed state in FIG. 5B and the applied force shown in FIG. 5A, in accordance with embodiments of the present disclosure;

FIG. 5C depicts a perspective view of the collapsible floral menstrual cup of FIG. 5A transferred from the open state in FIG. 5A to a closed state with closed flaps and collapsed basin through pulling and twisting force, in accordance with embodiments of the present disclosure;

FIG. 6A depicts an illustrative view of an insertion of the collapsible floral menstrual cup of FIG. 1A with the assistive applicator of FIG. 3A, in accordance with embodiments of the present disclosure;

FIG. 6B depicts an illustrative view of the collapsible floral menstrual cup of FIG. 6A in an open state following insertion, in accordance with embodiments of the present disclosure;

FIG. 6C depicts an illustrative view of the collapsible floral menstrual cup of FIG. 6B in a closed state and prior to removal, in accordance with embodiments of the present disclosure;

FIG. 7A depicts a perspective view of a collapsible cradle menstrual disc including a tension-string wrapped around a disc body in an open state, in accordance with embodiments of the present disclosure;

FIG. 7B depicts a perspective view of the collapsible cradle menstrual disc of FIG. 7A in a closed state, in accordance with embodiments of the present disclosure;

FIG. 7C depicts an assistive applicator including a magnetic attaching mechanism used to contain and apply the collapsible cradle menstrual disc of FIG. 7B, in accordance with embodiments of the present disclosure;

FIG. 8A depicts an illustrative view of an insertion of the collapsible menstrual disc of FIG. 7A with the assistive applicator of FIG. 7C, in accordance with embodiments of the present disclosure;

FIG. 8B depicts an illustrative view of the collapsible menstrual disc of FIG. 7A in an open state following insertion, in accordance with embodiments of the present disclosure;

FIG. 8C depicts an illustrative view of the collapsible menstrual disc of FIG. 8B in a closed state and prior to removal, in accordance with embodiments of the present disclosure;

FIGS. 9A-9C depict a process of inserting the collapsible floral menstrual cup of FIG. 1A, in accordance with embodiments of the present disclosure;

FIGS. 9D-9F depict a process of inserting the collapsible cradle menstrual disc of FIG. 7A, in accordance with embodiments of the present disclosure;

FIG. 10A depicts a perspective view of a collapsible menstrual cup with a cap in a closed state, in accordance with embodiments of the present disclosure;

FIG. 10B depicts a cross-sectional view of the collapsible menstrual cup of FIG. 10A in a closed state, in accordance with embodiments of the present disclosure;

FIG. 11A depicts a cross-sectional schematic of the collapsible menstrual cup of FIG. 10A in an open state, in accordance with embodiments of the present disclosure;

FIG. 11B depicts a cross-sectional schematic of the collapsible menstrual cup of FIG. 11A in a closed state, in accordance with embodiments of the present disclosure; and FIG. 11C depicts a bottom plan view of a cap and stem of the collapsible menstrual cup of FIG. 11A, in accordance with embodiments of the present disclosure.

DETAILED DESCRIPTION

The present disclosure generally relates to collapsible a menses collecting apparatus for receiving, collecting, and safely containing menses discharged during menstrual period. FIGS. 1-11C in general depict menstrual cups designed to collecting menses, in accordance with embodiments of the present disclosure. FIGS. 1-6C and 9A-9C depict collapsible floral menstrual cup devices including a collapsible basin with multiple foldable flaps, whereas FIGS. 7A-8C and 9D-9F depicts collapsible cradle menstrual disc devices with a foldable body. A comparison of the processes in FIGS. 9A-9C versus 9D-9F illustrate how the different cup designs of FIGS. 1-6C versus 7A-8C may impact users' wearing experience. Further, FIGS. 10A-11C depict a menstrual cup device with a flexible membrane including an opening into a basin or cavity, and a cap operable to engage with the flexible membrane to provide or prevent access to the basin or cavity through the opening in the flexible membrane. Through a tension-based mechanism, the collapsible a menses collecting apparatuses in the present disclosure allow users to readily apply the a menses collecting apparatuses without excessive twisting and adjusting of the position by hand. In addition, the collapsible menstrual cups of the present disclosure are capable of automatic closure avoiding collected menses spilling out during the removal process. Further, the collapsible a menses collecting apparatuses in the present disclosure are equipped with the abovementioned improvements without interfering with traditional menstrual cups' reusable features.

In some non-limiting examples, the cup and/or disc embodiments may be manufactured to conform to known anthropometric data for (e.g., for the $50^{th}$ percentile, the $95^{th}$ percentile, or the like of users). Table 1 provides example ranges for the body length, total length, diameter, and capacity of the various cup and disc embodiments for the menses collecting apparatuses as described throughout the present disclosure.

TABLE 1

| Example dimension ranges for menstrual cup and disc embodiments | | |
| --- | --- | --- |
| | CUP | DISC |
| Length (body) | 1.22-3.07 inches (in) | 0.79-1.97 in |
| | 31-78 millimeters (mm) | 20-50 mm |
| Length (total) | 2.17-3.07 in | 0.79-1.97 in |
| | 55-78 mm | 20-50 mm |
| Diameter | 1.22-2.09 in | 2.09-3.15 in |
| | 31-53 mm | 53-80 mm |
| Capacity | 0.34-1.35 ounces (oz) | 1.01-2.37 oz |
| | 10-40 milliliters (mL) | 30-70 mL |

FIG. 1 depicts a collapsible floral menstrual cup 100, in accordance with embodiments of the present disclosure. It is noted that embodiments directed to the floral cup 100 may be applicable to a cradle disc 700 and/or a menstrual cup 1000 as described in detail herein, and vice versa, unless otherwise noted without departing from the scope of the present disclosure.

The collapsible menstrual cup 100 includes a basin 102 with basin walls 104 and a closure 106 with one or more flaps 108. FIGS. 2A-2B are perspective views of the collapsible floral menstrual cup 100 of FIG. 1 in an expanded and open state 202 and an expanded and closed state 204, respectively. In particular, FIG. 2A is a perspective view of a collapsible floral menstrual cup 100 in the open state 202, where the flaps 108 are open (or in an open configuration) and exposing a basin cavity 206 defined by the basin walls 104 and/or one or more flaps 108 of the closure 106 for receiving menses. In addition, FIG. 2B is a perspective view of the floral collapsible menstrual cup 100 in the closed state 204, where the flaps 108 are closed (or in a closed configuration) allowing the basin cavity 206 to contain collected menses securely.

In some embodiments, the basin walls 104 transition between a collapsed or folded state and a non-collapsed or unfolded state. For example, when the basin 102 is in a collapsed or folded state, the cup 100 may be insertable. By way of another example, when the basin 102 is in the non-collapsed or unfolded state, access may be provided to the basin cavity 206 defined within the basin walls 104 forming the basin 102. The basin cavity 206 is fluid-tight when in either state (e.g., due to the material from which the basin walls 104 of the basin 102 is fabricated, as described throughout the present disclosure), and is also operable to receive menses when the basin 102 is in the non-collapsed or unfolded state. It is noted the basin 102 may be insertable or removable either in the collapsed or folded state (e.g., prior to collecting menses) or in the non-collapsed or unfolded state (e.g., where the defined basin cavity 206 has collected menses and is set for removal).

The basin 102 includes a ring 208 (e.g., rim) configured to form a seal with (or against) a vaginal wall when inserted. For example, the ring 208 may be complete, such that menses does not leak between the ring and the vaginal wall, rendering the cup 100 fluid-tight against the vaginal wall. In example embodiments where the ring 208 is substantially circular in shape and/or substantially conformable into a circular shape (e.g., due to flexibility and forces applied on the ring by the vaginal wall), the seal may be substantially circumferential. However, it is noted that the ring 208 may be non-circular in shape, but instead may be formed to more closely approximate a particular anatomy of a user to provide that user with increased comfort.

In some embodiments, the closure 106 is coupled to the basin 102 at or proximate to the ring 208 of the basin 102. The closure 106 may include the one or more flaps 108, which are actuatable between the open state 202 and the closed state 204.

A tension-based mechanism 210 communicates with both the basin 102 and the closure 106. The tension-based mechanism 210 includes or is in communication with an activator 212 (e.g., stem, ring, string, or other actuatable device) for the convenience of users to control the collapsible menstrual cup 100. Upon applying an appropriate force on the activator 212, the closure 106 may transition between the first and second states (e.g., open state 202 and closed state 204). In the present disclosure, pulling and/or pushing the activator 212 activates the tension-based mechanism 210 to cause a transition between the first state and the second state.

For example, as depicted in FIG. 2A, the flaps 108 may be open in the first state 202. Although not shown, it is contemplated the flaps 108 may extend from the rim 208 and have an exterior or outer surface 209 that at least partially touches the vaginal wall. Alternatively, the flaps 108 may extend from the rim 208 of the basin 102 and into the vaginal canal without touching the vaginal wall. By way of another example, as depicted as FIG. 2B, the flaps 108 may be closed in the second state 204. The flaps 108 may at least partially overlap when in the second state 204. Alternatively, the flaps 108 may abut against one another when in the second state 204. It is noted that FIGS. 6B and 6C illustrate an example insertion of the menstrual cup 100 within a user.

FIGS. 3A-3C generally illustrate a system 300 including a collapsible floral menstrual cup 100 operable to be inserted and/or activated by an assistive applicator 302, in accordance with one or more embodiments of the present disclosure. As depicted in FIGS. 3A-3C, the menstrual cup 100 is operable to transition between a folded and collapsed state 310, the expanded and open state 202, and the expanded and closed state 204. During the transition, the menstrual cup 100 is operable to receive menses in the open state 202 and contain menses in the closed state 204.

As shown in FIG. 3A, the applicator 302 includes a handle 304, one or more applicator walls 306, and an applicator cavity 308 used to store the menstrual cup 100. For example, in the present disclosure, the applicator 302 stores the collapsible menstrual cup 100 at its folded and collapsed state 310. The applicator 302 may further receive the menstrual cup 100 at its folded and collapsed state 310 and store the menstrual cup 100 for next use.

As shown in FIG. 3B, the menstrual cup 100 includes the tension-based mechanism 210 to assist in actuating or transitioning a basin 102 and/or a closure 106 between various states. The tension-based mechanism 210 may provide a method to a user to position, adjust, unfold, and/or collapse the basin 102 and/or the closure 106 when inserted. The tension-based mechanism 210 communicates with both the basin 102 and the closure 106. The tension-based mechanism may include an activator 212 (e.g., steam, ring, string, or other actuatable device) for the convenience of users to control the collapsible menstrual cup 100. Upon applying an appropriate force on the activator 212, the closure 106 may transition between the first and second states (e.g., open state 202 and closed state 204). In the present disclosure, pulling and/or pushing the activator 212 activates the tension-based mechanism 210 to cause transition between the first state and the second state.

Pushing the handle 304 may cause the basin 102 to expand from the collapsed position 310 to the open state 202 and form a seal with the vaginal wall. The activator 212 may cause the basin 102 to actuate or transition between the open state 202 and the closed state 204 or the collapsed state 310. For example, FIG. 3C illustrates that when a user pulling the activator 212, the pulling force may cause the basin 102 to fold into the closed position 204. Such a pulling force applied on the activator 212 may further cause the basin 102 to break a seal between a rim 208 and the vaginal wall.

It is noted the embodiments depicted in FIGS. 2A-2D and 3A-3C represent a tension-based mechanism for operating the menstrual cup 100. Applying a force to the activator 212 causes the activator 212 to pull on the flaps 108, actuating the flaps 108 to close the menstrual cup 100. For example, the applied force may be a downward-pulling motion on the activator 212 that translates to a downward-pulling force on the flaps 108, bending the flaps 108 inward over the basin 102.

FIGS. 4A-4D in general depict a system 300 including the assistive applicator 302 and a collapsible menstrual cup 100 guided by the assistive applicator 302, in accordance with embodiments of the present disclosure. As depicted in FIGS. 4A-4D, the menstrual cup 100 is operable to transition between the folded and collapsed state 310, the expanded and open state 202, and the expanded and closed state 204. During the transition, the menstrual cup 100 is operable to receive menses in the open state 202 and contain menses in the closed state 204.

Referring now to FIG. 4A, the applicator 302 includes an applicator cavity 308 defined within applicator walls 306. For example, the menstrual cup 100 may be loaded in the applicator cavity 308 prior to insertion by a user, and may transport the menstrual cup 100 to a correct placement within the vagina of the user. The applicator 302 may then leave the menstrual cup at the correct placement while being removed. It is noted that FIG. 6A illustrates an example insertion of a menstrual cup with the applicator.

The applicator cavity 308 may be operable to receive the collapsed menstrual cup 100 in guided form when the menstrual cup 100 is in fully folded and collapsed state 310 within the applicator 302, where the folded basin walls 104 may be configured to conform to the sides of the applicator cavity 308 when the menstrual cup 100 is in the collapsed form 310. It is noted the guided form may reduce the risk of the menstrual cup 100 failing to unfold or deploy during insertion and placement, and/or shifting from the correct or intended placement during the unfolding process due to the controlled unfolding that may occur with the guided form of the applicator cavity 308.

It Is noted, however, that the applicator 302 may also be operable to receive the collapsed menstrual cup 100 in non-guided form when the menstrual cup 100 is in the folded state 310 within the applicator 302, where the folded basin walls 104 are not configured to conform to the sides of the applicator cavity 308 when the menstrual cup is in the collapsed form 310, without departing from the scope of the present disclosure. It is noted the nonguided design for the applicator 302 may be cheaper to manufacture and produce, while also reducing a risk that the menstrual cup 100 gets stuck in the applicator during insertion and placement.

Once inserted into the vagina, the applicator 302 may be removed and the menstrual cup 100 may be deposited within the vagina. During the depositing, the collapsed menstrual cup 100 may automatically transition from the collapsed state 310 to the open state 202 as it exits the applicator 302. For example, in FIG. 4A, the menstrual cup 100 may be stored fully within or extend at least partially from the applicator 302 in the state 310, where the menstrual cup 100 is folded and collapsed in a thin form. Once the menstrual cup 100 exits and/or is fully removed from the applicator 302, the menstrual cup 100 automatically expands to the open state 202 with the flaps 108 opened and the basin 102 expanded. In the open state 202, the menstrual cup 100 is ready to receive menses.

It Is noted the applicator 302 may include a handle 304 or other component configured to assist in insertion, adjustment, and removal of the applicator during application of the menstrual cup 100. It is noted the handle 304 may include a release mechanism configured to retain the menstrual cup 100 within the applicator 302 during insertion and adjustment, which may release the menstrual during removal of the applicator. For example, the handle 304 may be operable to engage with the activator 212 or other component of the menstrual cup 100 while the menstrual cup 100 is positioned within the applicator cavity 308.

Although embodiments are directed to the use of an applicator 302 to insert the menstrual cup 100 in the collapsed state, it will be appreciated that the collapsed menstrual cup 100 may be inserted by a user without the use of an applicator 302, without departing from the scope of the present disclosure. In this regard, use of the applicator is not intended to be limiting on the present disclosure.

Referring in general to the transition depicted in FIGS. 4B-4D, the tension-based mechanism 210 may assist in actuating or transitioning the unfolded menstrual cup 100 between the open state 202 and the closed state 204. In particular, FIG. 4B illustrates the menstrual cup 100 in the expanded and open state 202 after insertion, FIG. 4C illustrates the menstrual cup 100 receiving menses while in the expanded and open state 202 when inserted, and FIG. 4D illustrates the menstrual cup 100 in the expanded and closed state 204 (e.g., after receiving the menses), where the tension-based mechanism 210 was employed by the user to transition the menstrual cup 100 between the open state 202 and the closed state 204.

The tension-based mechanism 210 may include a stabilizing mechanical device which causes the closure to remain in the open state 202 or the closed state 204 unless acted upon by the tensioned-mechanism 210. The mechanical device may be installed within the basin 102 and/or the closure 106 (e.g., a spring, detent, tab-and-groove assembly, stops as illustrated in FIGS. 10A-11C, or other installed component). The stabilizing mechanical device may be integrated into the design of the basin 102 and/or the closure 106 (e.g., a living hinge, or the like). In this regard, the open state 202 and/or the closed state 204 may be considered stable, for purposes of the present disclosure.

By way of another example, pushing on the activator 212 may cause the closed closure to begin to open. An opposing force is exerted against the activator 212 by the mechanical device until a predefined point in the transition from the closed state 204 to the open state 202 is achieved. At which point, the opposing force is no longer applied, and an assistive force is instead applied by the mechanical device, which may be standalone or combined with the pushing motion, to complete the transition from the second state to the first state.

FIGS. 5A-5C illustrate a collapsible menstrual cup 100 turning downward force into torsional and/or transverse force, pulling the flaps 108 inward, breaking the seal and closes the cup's opening, in accordance with embodiments of the present disclosure. In particular, FIG. 5A illustrates a perspective view of the menstrual cup 100 in the open state 202, FIG. 5B illustrates a top view of the menstrual cup 100 in the open state 202, and FIG. 5C illustrates a perspective view of the menstrual cup 100 in the closed state 204.

Through the tension-based mechanism, pulling on the activator 212 may cause the open state 202 to begin to close. An opposing force is exerted against the activator 212 by the mechanical device until a predefined point in the transition from open state 202 with the expanded basin 102 and open flaps 108 to the closed state 204 with the expanded basin 102 and closed flaps 108. FIG. 5A further illustrates the process and force distribution 500 via which the menstrual cup 100 is closing and collapsing while a pulling force is applied on the activator 212. Further, the flaps 108 may overlap with each other allowing secured containment of menses.

It is noted the embodiments depicted in FIGS. 4A-4D and 5A-5C represent a tension-based mechanism for operating the menstrual cup 100. Applying a force to the activator 212 causes the activator 212 to pull on the flaps 108, actuating the flaps 108 and closing the menstrual cup 100. For example, the applied force may be a downward-pulling motion on the activator 212 that is converted into a rotational force or transverse force via an internal screw mechanism within the menstrual cup 100 that ties or sinches the flaps 108 closed (e.g., similar to a drawstring bag) to cover the basin cavity 206.

FIGS. 6A-6C in general depict a process of utilizing the system 300 including the applicator 302 and the collapsible floral menstrual cup 100, in accordance with embodiments of the present disclosure. In particular, FIGS. 6A-6C illustrate the supplying of the collapsible menstrual cup 100 via the companion applicator 302 and positioning the menstrual cup 100 in FIGS. 6A and 6B, and taking out the collapsible menstrual cup 100 in FIG. 6C.

As shown in FIG. 6A, to apply the collapsible menstrual cup 100, a user may insert the applicator 302 containing a menstrual cup in a folded form into their vagina. Once the user has adjusted the applicator 302 to an appropriate and comfortable position, the user may push the handle 304 to deposit the menstrual cup 100 within their vagina. A user will then disengage the applicator 302 from the menstrual cup 100 by controlling the handle 304 of the applicator 302 and/or the tension-based mechanism 210 of the menstrual cup 100.

As shown in FIG. 6B, during or after the applicator disengages the menstrual cup 100, the menstrual cup 100 expands to the open state 202 and the flaps 108 may be open in the first state 202, either extended from the rim 208 of the basin 102 and at least partially touching the vaginal wall or alternatively extended from the rim 208 of the basin 102 and into the vaginal canal without touching the vaginal wall.

As shown in FIG. 6C, to take out the menstrual cup 100 from the vaginal area, a user may pull the activator 212 (i.e., a stem, a ring, a string, or other actuatable device). The menstrual cup 100 will turn the pulling force into a torsional and/or transverse force, resulting in the flaps 108 and/or basin 102 to collapse, sealing menses inside the menstrual cup cavity 206.

FIGS. 7A-7C depicts a collapsible cradle menstrual disc 700, in accordance with embodiments of the present disclosure. It is noted that embodiments directed to the cradle disc 700 may be applicable to the floral cup 100 and/or a menstrual cup 1000 as described in detail herein, and vice versa, unless otherwise noted without departing from the scope of the present disclosure.

In embodiments, the collapsible cradle menstrual disc 700 includes a body 702 and a disc-control mechanism 704 (e.g., a tension-string wrapped around the body 702). Specifically, the body 702 comprises a disc basin 706 with defined cavity 708, a disc rim 710, and a disc closure 712. When activated, the menstrual disc 700 will transfer into an open state 714 (FIG. 7A, wherein the disc basin 706, the rim 710, and the closure 712 defines the cavity 708. The disc-control mechanism 704 includes an activator 716 and a tension string 718. As shown in FIG. 7A, the body 702 is construed in a single-piece structure.

The tension string 718 is attached to the body 702 so that when a user applies a pulling force to the activator 716, the tension string 718 will transfer the force to the disc portion resulting in the disc opening closing and sealing menses inside the cavity 708 for a clean, hassle-free removal. For example, pulling down on the activator 716 pinches the sides of the body 702 inward, closing the disc basin 706 similar to a coin purse. In some embodiments, the flap and/or closure 712 may be attached to the tension string 718 to achieve a better menses sealing effect. In this regard, the menstrual disc 700 may be folded to fit within the applicator 720, decreasing a diameter of the menstrual disc 700 and keeping collected menses contained within the body 702.

In some embodiments, an applicator 720 is provided for easy application of the menstrual disc 700. The applicator 720 includes a plunger or handle 722, and a menstrual disc container or applicator walls 724. In some embodiments, a pair of connecting components 726 and 728 are installed on the applicator 720 and the cradle menstrual disc 700. For example, the connecting components 726, 728 may include magnets in the applicator 720 and the disc 700. In general, the connecting components 726 and 728 may be considered components of an interlocking assembly 729, wherein the interlocking assembly 729 includes any components that interact with one another (e.g. magnets) and/or have corresponding features that interlock with one another (e.g., tab-and-slot, protrusion-and-groove, or the like). It is noted that any of the systems described throughout the present disclosure including a menses collecting apparatus and an activator may or may not include an interlocking assembly 729, without departing from the scope of the present disclosure.

In one example embodiment, as shown in FIG. 7C, the first component 726 is installed on the applicator 720 located at the bottom of the container 724. The first component 726 is also connected to the plunger 722 so that the first component 726 may move along with the plunger 722 inside the container 724. The second component 728 in installed on the menstrual disc 700 (e.g., at the bottom or distal end of the activator 716).

When the menstrual disc 700 is stored inside the applicator 720, the first and the second components 726, 728 will contact each other. When using a magnetic material (e.g., selected from a group including iron, cobalt, nickel, and magnetic alloys, and the like) for the first and second components, the applicator 720 can secure the menstrual disc 700 and guide the menstrual disc 700 during the process of applicating and positioning the menstrual disc 700. Further, the magnetic force can assist the applicator 720 in receiving the menstrual disc 700 back from the vagina. It is noted that the menstrual disc 700 and the applicator 720 may be considered a system 730, for purposes of the present disclosure. In addition, it is noted that the components 726, 728 such as magnets, or the like may be installable and usable with the system 300 including the cup 100 and the applicator 302, without departing from the scope of the present disclosure.

FIGS. 8A-8C in general depict a process of utilizing the system 730 including the applicator 720 and the collapsible menstrual disc 700, in accordance with embodiments of the present disclosure. In particular, FIGS. 8A-8C illustrate the supplying of the collapsible menstrual disc 700 via the companion applicator 720 and positioning the menstrual disc 700 in FIGS. 8A and 8B, and taking out the collapsible menstrual disc 700 in FIG. 8C.

As shown in FIG. 8A, to apply the collapsible menstrual disc 700, a user may insert the applicator 720 containing a menstrual disc 700 in a folded form into their vagina. Once the user has adjusted the applicator 720 to an appropriate and comfortable position, the user may deposit the menstrual disc 700 within their vagina. A user will then disengage the applicator 720 from the menstrual disc 700.

As shown in FIG. 8B, during or after the applicator disengages the menstrual disc 700, the menstrual disc 700 expands to an open state 802 and the disc basin 706 may be open in the first state 802, either at least partially touching the vaginal wall or alternatively extended into the vaginal canal without touching the vaginal wall.

As shown in FIG. 8C, to take out the menstrual disc 700 from the vaginal area, a user may pull the activator 716 (i.e., a stem, a ring, a string, or other actuatable device). The menstrual disc 700 will pinch the opposite long-sides of the disc basin 706 together in response to the pulling force, resulting in the disc basin 706 transitioning into a closed state 804 and sealing menses inside the menstrual cup cavity 708.

FIGS. 9A-9C and 9D-9F depict a comparison of the installation of collapsible menstrual cup 100 and disc 700, in accordance with embodiments of the present disclosure. In particular, FIGS. 9A-9C shows a process of inserting the cup 100, whereas FIGS. 9D-9F shows a process of inserting the disc 700. Compared to the cup 100 with the floral design demonstrated in FIGS. 9A-9C, the disc 700 with the cradle design illustrated in FIGS. 9D-9F has a wider diameter allowing the menstrual disc 700 to sit farther back towards the cervix. In addition, the floral cup 100 may be inserted by folding or squishing the cup rim into a collapsed state prior to insertion that expands into an unfolded state after insertion, whereas the disc 700 is pinched along opposite long-edges like a coin purse. In this regard, the disc 700 is inserted sideways, whereas the cup 100 is inserted top-first. This difference in operation causes the disc 700 to be easier to insert in some instances, by only needing to pinch opposing long-edges of the disc 700 during insertion as opposed to folding and maintaining the folded state of the cup 100 during insertion. Both the floral cup 100 and the cradle disc 700, however, allow the rim and/or basin contact with the vaginal wall and ensure safe sealing of menses without leakage during usage.

FIGS. 10A-10B depicts a collapsible menstrual cup 1000 with a cap 1010, in accordance with embodiments of the present disclosure. It is noted that embodiments directed to the menstrual cup 1000 may be applicable to the floral cup 100 and/or the cradle disc 700 as described in detail herein, and vice versa, unless otherwise noted without departing from the scope of the present disclosure.

The collapsible menstrual cup 1000 includes a basin 1002 with basin walls 1004 and a closure or membrane 1006 with one or more flaps 1008. In some examples, the flaps 1008 may be flexible or bendable, semi-rigid, or rigid. It is noted that "closure" and "membrane" are interchangeable throughout the present disclosure.

A cap 1010 positioned proximate to the membrane 1006 is operable to provide or prevent access to a cavity 1012 defined within the basin walls 1004. FIGS. 11A-11B are perspective views of the collapsible menstrual cup 1000 of FIGS. 10A-10B in an expanded and open state 1102 and an expanded and closed state 1104, respectively. In particular, FIG. 11A is a perspective view of a collapsible menstrual cup 1000 in the open state 1102, where the cap 1010 is open (or in an open configuration) and exposing the basin cavity 1012 defined by the basin walls 1004 and/or one or more flaps 1008 of the membrane 1006 for receiving menses. In addition, FIG. 11B is a perspective view of the collapsible menstrual cup 1000 in the closed state 1104, where the flaps 1008 are closed (or in a closed configuration) allowing the basin cavity 1012 to contain collected menses securely.

In some embodiments, the basin walls 1004 transition between a collapsed or folded state and a non-collapsed or unfolded state. For example, when the basin 1002 is in a collapsed or folded state, the cup 100 may be insertable. By way of another example, when the basin 1002 is in the non-collapsed or unfolded state, access may be provided to the basin cavity 1012 defined within the basin walls 1004 forming the basin 1002. The basin cavity 1012 is fluid-tight when in either state (e.g., due to the material from which the basin walls 1004 of the basin 1002 is fabricated, as described throughout the present disclosure), and is also operable to receive menses when the basin 1002 is in the non-collapsed or unfolded state. It is noted the basin 1002 may be insertable or removable either in the collapsed or folded state (e.g., prior to collecting menses) or in the non-collapsed or unfolded state (e.g., where the defined basin cavity 1012 has collected menses and is set for removal).

The basin 1002 includes a ring 1014 (e.g., rim) configured to form a seal with (or against) a vaginal wall when inserted. For example, the ring 1014 may be complete, such that menses does not leak between the ring and the vaginal wall, rendering the cup 1000 fluid-tight against the vaginal wall. In example embodiments where the ring 1014 is substantially circular in shape and/or substantially conformable into a circular shape (e.g., due to flexibility and forces applied on the ring by the vaginal wall), the seal may be substantially circumferential. However, it is noted that the ring 1014 may be non-circular in shape, but instead may be formed to more closely approximate a particular anatomy of a user to provide that user with increased comfort.

In some embodiments, the membrane 1006 is coupled to the basin 1002 at or proximate to the ring 1014 of the basin 1002. The membrane 1006 may include the one or more flaps 1008, which are actuatable between the open position 1102 and the closed position 1104.

A tension-based mechanism 1016 communicates with both the basin 1002 and the membrane 1006. The tension-based mechanism 1016 includes or is in communication with an activator 1018 (e.g., stem, ring, string, or other actuatable device) for the convenience of users to control the collapsible menstrual cup 1000. Upon applying an appropriate force on the activator 1018, the membrane 1006 may transition between the first and second states (e.g., open state 1102 and closed state 1104). In the present disclosure, pulling and/or pushing the activator 1018 activates the tension-based mechanism 1016 to cause a transition between the first state and the second state. It is noted that the cap 1010 may be considered part of or alternatively coupled to the tension-based mechanism 1016.

For example, as depicted in FIG. 11A, the flaps 1008 may be open in the first state 1102. By way of another example, as depicted as FIG. 2B, the flaps 1008 may be closed in the second state 1104. The flaps 1008 may be separated by the activator 1018 when in the second state 1104. Alternatively, at least a portion of the flaps 108 may abut against one another when in the second state 1104. Further, it is noted that the flaps 1008 may be symmetrical or asymmetrical in forming the membrane 1006, without departing from the scope of the present disclosure.

It is noted that the flaps 1008 may be planar (e.g., within a same defined plane) when the cap 1010 is in the open configuration 1102, or may be within different defined planes when the cap 1010 is in the open configuration 1102, without departing from the scope of the present disclosure. Alternatively, it is noted that the flaps 1008 may be planar (e.g., within a same defined plane) when the cap 1010 is in the closed configuration 1104, or may be within different defined planes when the cap 1010 is in the closed configuration 1104, without departing from the scope of the present disclosure.

As illustrated in FIGS. 10B, 11A, and 11B, the activator 1018 is coupled to or integrated with the cap 1010, such that applying a force to the activator 1018 transfers the force to the cap 1010. The activator 1018 includes one or more stops 1020. For example, as illustrated in FIG. 11A, the activator 1018 may include a first stop 1020 that holds the cap 1010 in an open position within the open state 1102, providing access for menses to enter the cavity 1012 via an opening 1022 within the membrane 1006 surrounded by the flaps 1008. By way of another example, as depicted in FIG. 11B, the activator 1018 may include a second stop 1020 that holds the cap 1010 in a closed position within the closed state 1104, sealing the cavity 1012 and preventing access to cavity 1012 by menses.

Referring now to FIG. 11C, in some embodiments the cap 1010 may include one or more raised protrusions 1024 that lift a body 1026 of the cap 1010 from the upper surfaces of the membrane 106/flaps 1008. The protrusions 1024 encompass or form one or more grooves 1028 within the cap 1010. For example, the one or more grooves 1028 may allow for menses to flow into the cavity 1012 when the cap 1010 is in the open state 1102, while the protrusions 1024 may correctly positioned the cap 1010 against the flaps 1008 of the membrane 1006.

In some embodiments, the cap body 1026 includes one or more stops 1106 that engage with the flaps 1008 of the membrane 1006 when the cap 1010 is in the closed state 1104. For example, the one or more stops 1106 may prevent menses flow through the opening 1022 when the cap 1010 is in the closed state 1104.

It is noted the embodiments depicted in FIGS. 10A-10B and 11A-11C represent a tension-based mechanism for operating the menstrual cup 1000. Applying a force to the activator 1018 causes the activator 1018 to act on the cap 1010 to close the opening 1022 to the cavity 1012 in the menstrual cup 1000. For example, the applied force may be a downward-pulling motion on the activator 1018 that causes at least a portion of the cap 1010 to pass through the opening 1022, thus closing the opening 1022 and containing the collected menses within the 1012. It is noted that the downward force being applied on the membrane 1006 by the cap 1010 when in the closed position may cause the sidewalls 1004 of the basin 1002 to draw together, reducing a diameter of the basin 1002 (e.g., as illustrated in FIG. 11B).

One or more of the menstrual cups or the applicator may be formed from an antimicrobial plastic, a medical grade silicone, or a suitable paper, fabric, or rubber, or other material which may be safely inserted without risk of injury, infection, or other harm to the user.

In embodiments, a cleaning kit is contemplated. The cleaning kit may be provided with the applicator and/or the menses collecting apparatuses 100, 700, 1000 as described throughout the present disclosure. It is noted the menses collecting apparatus 100, 700, 1000, the applicator, and/or the cleaning kit may be considered components of a female hygiene system, for purposes of the present disclosure. In addition, it is noted the female hygiene system may include or be operable with microwave-safe containers and/or home sonication devices. Further, it is noted the female hygiene system may include or be operable with a hard case able to receive a filled apparatus 100, 700, 1000. The hard case may include at least one inlet operable to receive a fluid and/or at least one outlet operable to expel a fluid. For example, the case may include valves that allow water or other cleaning fluid to flow into the case to at least partially surround the apparatus 100, 700, 1000. By way of another example, the case may include valves that allow for the expelling of water/cleaning fluid, menses, or a combination thereof. In this regard, primary washing of the apparatus 100, 700, 1000 may occur within the container.

Advantages of the present disclosure are directed to a novel and non-obvious menses collecting apparatus. The apparatus is a cup that is able to transition between a folded and collapsed state, an expanded and open state, and an expanded and closed state. In some embodiments, the folded and collapsed state allows for increased ease of installation by a user, either manually with the assistance of an applicator. In addition, the expanded and open state provides an increased level of sealing against the vaginal wall to prevent leakage of menses. Further, the expanded and closed state provided an increased level of containment of menses to prevent leakage during removal of the cup. Through a tension-based mechanism, the menses collecting apparatus in the present disclosure allow users to readily apply the cups without excessive twisting and adjusting of the position by hand, reducing possible injury to the user. In addition, the menses collecting apparatus of the present disclosure are capable of automatic closure avoiding collected menses spilling out during the removal process. Further, the menses collecting apparatus in the present disclosure are equipped with the abovementioned improvements without interfering with traditional menstrual cups' reusable features. As such, the apparatus provides a solution to a long-felt but unmet need for improved menses collection in a reusable and environment-friendly package, as compared to existing pads or tampons currently known.

While various embodiments of the present disclosure have been described in detail, it is apparent that modifications and alterations of those embodiments will occur to those skilled in the art. However, it is to be expressly understood that such modifications and alterations are within the scope and spirit of the present disclosure. Further, the invention(s) described herein are capable of other embodiments and of being practiced or of being carried out in various ways. In addition, it is to be understood that the phraseology and terminology used herein is for the purposes of description and should not be regarded as limiting.

The foregoing examples of the present disclosure have been presented for purposes of illustration and description. These examples are not intended to limit the disclosure to the form disclosed herein. Consequently, variations and modifications commensurate with the teachings of the description of the disclosure, and the skill or knowledge of the relevant art, are within the scope of the present disclosure. The specific embodiments described in the examples provided herein are intended to further explain the best mode known for practicing the disclosure and to enable others skilled in the art to utilize the disclosure in such, or other, embodiments and with various modifications required by the particular applications or uses of the present disclosure. It is intended that the appended claims be construed to include alternative embodiments to the extent permitted by the prior art.

What is claimed is:

1. A menses collecting apparatus, comprising:
a basin for collecting menses, comprising:
   one or more basin walls; and
   a basin cavity defined within the one or more basin walls,
   wherein the basin is operable to receive and collect menses within the basin cavity when the apparatus is in a first stable state, and is operable to be removed while containing the collected menses within the basin cavity when the apparatus is in a second stable state;
a closure coupled to the basin; and
a tension-based mechanism including an activator, wherein the activator is operable to cause the apparatus to transition between an open configuration in which the basin cavity receives and collects the menses and a closed configuration operable to contain the menses within the basin cavity after the basin cavity receives and collects the collected menses.

2. The menses collecting apparatus according to claim 1, wherein the basin is open and expanded and the apparatus is in the open configuration in the first stable state, and wherein the basin is open and expanded and the apparatus is in the closed configuration in the second stable state.

3. The menses collecting apparatus according to claim 1, wherein the activator is coupled to the closure, wherein the closure folds during transition between the open configuration and the closed configuration at a location where the closure couples to the basin.

4. The menses collecting apparatus according to claim 3, wherein the closure comprises one or more flaps that fold downward during a transition from the open configuration to the closed configuration.

5. The menses collecting apparatus according to claim 3, further comprising a rim at the location where the closure couples to the basin.

6. The menses collecting apparatus according to claim 1, wherein the apparatus is operable to be inserted into a user in a third state, wherein the basin and the closure is folded and collapsed in the third state.

7. The menses collecting apparatus according to claim 6, wherein the tension-based mechanism is actuatable via the activator to cause the apparatus to transition from the third state to the first stable state, wherein the apparatus creates a seal with a vaginal wall of the user during the transition.

8. The menses collecting apparatus according to claim 7, wherein the tension-based mechanism is actuatable via the activator to cause the apparatus to transition from the first stable state to the second stable state, wherein the apparatus breaks the seal with the vaginal wall during the transition.

9. The menses collecting apparatus according to claim 7, wherein the basin forms a complete, substantially circumferential seal along vaginal walls when the first stable state.

10. The menses collecting apparatus according to claim 6, wherein the basin is collapsible radially to be folded and collapsed into the third state.

11. The menses collecting apparatus according to claim 6, wherein the apparatus is at least partially insertable into an applicator for use during insertion of the menses collecting apparatus into the user when in the third state.

12. The menses collecting apparatus according to claim 1, wherein the activator is a stem, a pulling ring, or a string.

13. The menses collecting apparatus according to claim 1, wherein the basin is a single-piece cup including the one or more basin walls.

14. The menses collecting apparatus according to claim 1, wherein the basin is a single-piece cradle-shaped disc including the one or more basin walls.

15. The menses collecting apparatus according to claim 1, further comprising:
a cap in communication with the activator, wherein the activator is operable to cause the cap to transition from an open position and a closed position, wherein the cap is configured to close an opening within the closure when the apparatus is in the closed configuration to contain the menses within the basin cavity after the basin cavity receives and collects the collected menses.

16. A system, comprising:
a menses collecting apparatus, comprising:
   a basin for collecting menses, comprising:
      one or more basin walls; and
      a basin cavity defined within the one or more basin walls,
      wherein the basin is operable to receive and collect menses within the basin cavity when the apparatus is in a first stable state, and is operable to be removed while containing the collected menses within the basin cavity when the apparatus is in a second stable state;
   a closure coupled to the basin; and
   a tension-based mechanism including an activator, wherein the activator is operable to cause the apparatus to transition between an open configuration in which the basin cavity receives and collects the menses and a closed configuration operable to contain the menses within the basin cavity after the basin cavity receives and collects the collected menses; and an applicator operable to receive the menses collecting apparatus when in a third state and insert the menses collecting apparatus into a user in the third state prior to the receiving and collecting of menses when the menses collecting apparatus is in the first stable state.

17. The system according to claim 16, wherein the applicator comprises a first connecting component and the menses collecting apparatus includes a corresponding second connecting component, wherein the first connecting component is operable to engage the corresponding second connecting component.

18. The system according to claim 17, wherein the first connecting component and the corresponding second connecting component are components of an interlocking assembly or are magnetic.

19. A method, comprising:

collecting menses with a menses collecting apparatus, wherein the menses collecting apparatus comprises:

a basin for collecting menses, comprising:

one or more basin walls; and a basin cavity defined within the one or more basin walls, wherein the basin in a first stable state, and wherein the basin is operable to receive and collect menses within the basin cavity when the apparatus is in the first stable state;

a closure coupled to the basin; and a tension-based mechanism including an activator, wherein the activator is operable to cause the apparatus to transition between an open configuration in which the basin cavity receives and collects the menses and a closed configuration operable to contain the menses within the basin cavity after the basin cavity receives and collects the collected menses; and actuating the tension-based mechanism via the activator to cause the menses collecting apparatus to transition from the first stable state to a second stable state, wherein the activator is operable to cause the apparatus to transition between the open configuration and the closed configuration, and wherein the basin is operable to be removed while containing the collected menses within the basin cavity when the apparatus is in the second stable state.

20. The method of claim 19, further comprising:

loading the menses collecting apparatus into an applicator prior to collecting the menses, wherein the menses collecting apparatus is in a third state when loaded into the applicator, and wherein the basin and the closure is folded and collapsed when the menses collecting apparatus in the third state.

* * * * *